United States Patent
Ertl et al.

(10) Patent No.: US 9,902,981 B2
(45) Date of Patent: Feb. 27, 2018

(54) PROCESS FOR THE PRODUCTION OF FURAN DERIVATIVES FROM GLUCOSE

(71) Applicant: ANNIKKI GMBH, Graz (AT)

(72) Inventors: Ortwin Ertl, Vasoldsberg (AT); Nicole Staunig, Vasoldsberg (AT); Marta Sut, Graz (AT); Bernd Mayer, Graz (AT); Marko Mihovilovic, Perchtoldsdorf (AT); Michael Schön, Vienna (AT); Johanna Hölbling, St. Georgen/Attergau (AT)

(73) Assignee: ANNIKKI GMBH, Graz (AT)

( * ) Notice: Subject to any disclaimer, the term of this patent is extended or adjusted under 35 U.S.C. 154(b) by 0 days.

(21) Appl. No.: 14/376,527

(22) PCT Filed: Feb. 6, 2013

(86) PCT No.: PCT/EP2013/052316
§ 371 (c)(1),
(2) Date: Aug. 4, 2014

(87) PCT Pub. No.: WO2013/117585
PCT Pub. Date: Aug. 15, 2013

(65) Prior Publication Data
US 2015/0010965 A1    Jan. 8, 2015

(30) Foreign Application Priority Data

| Feb. 7, 2012 | (EP) | 12450007 |
| Sep. 3, 2012 | (EP) | 12182758 |
| Sep. 12, 2012 | (WO) | PCT/EP2012/067781 |
| Dec. 10, 2012 | (AT) | A 1284/2012 |

(51) Int. Cl.
| C12P 17/04 | (2006.01) |
| C12P 19/02 | (2006.01) |
| C12P 41/00 | (2006.01) |
| C13K 11/00 | (2006.01) |
| C07D 307/46 | (2006.01) |
| C07D 307/68 | (2006.01) |
| C07D 307/50 | (2006.01) |

(52) U.S. Cl.
CPC ............ *C12P 17/04* (2013.01); *C07D 307/46* (2013.01); *C07D 307/50* (2013.01); *C07D 307/68* (2013.01); *C12P 19/02* (2013.01); *C12P 41/002* (2013.01); *C13K 11/00* (2013.01)

(58) Field of Classification Search
None
See application file for complete search history.

(56) References Cited

U.S. PATENT DOCUMENTS

| 295,022 A | 3/1884 | LaRock |
| 3,616,221 A | 10/1971 | Takasaki et al. |
| 3,868,304 A | 2/1975 | Messing |
| 4,467,033 A | 8/1984 | Horwath et al. |
| 4,895,601 A | 1/1990 | Binder et al. |
| 5,047,088 A | 9/1991 | Liaw et al. |
| 5,221,478 A | 6/1993 | Dhingra et al. |
| 7,163,815 B2 | 1/2007 | Riebel-Bommarius et al. |
| 2006/0035353 A1 | 2/2006 | Zhao et al. |
| 2012/0003688 A1 | 1/2012 | Bommarius et al. |

FOREIGN PATENT DOCUMENTS

| DE | 10247147 | 4/2004 |
| DE | 60006330 | 8/2004 |
| DE | 69839381 | 6/2009 |
| EP | 1152054 | 11/2001 |
| EP | 1285962 | 2/2003 |
| WO | WO86/04353 | 7/1986 |
| WO | WO2007118644 | 10/2007 |
| WO | WO2009076627 | 6/2009 |
| WO | WO2009/121785 | 10/2009 |
| WO | WO2011/124639 | 10/2011 |
| WO | WO2012/015616 | 2/2012 |
| WO | WO2013117251 | 8/2013 |

OTHER PUBLICATIONS

Yauda et al., "Transformation of Glucose to 5-Hydroxymethyl-2-furfural by Siox=MgCl2 Composite", Bull. Chem. Soc. Jpn. 2011, 84 (4), pp. 416-418.

Schrittwieser et al, "Recent biocatalytic oxidationreduction cascades", Current Opinion in Chemical Biology, vol. 15, No. 2, Apr. 11, pp. 249-256.

Suye et al. "Enzymatic production of 1-alanine from malic acid with malic enzyme and alanine dehydrogenase with coenzyme regeneration", The Canadian Journal of Chemical Engineering, vol. 70, No. 2, Apr. 1, 1992, pp. 306-312.

Voss et al: "Orchestration of Concurrent Oxidation and Reduction Cycles for Stereoinversion and Deracemisation of sec-Alcohols", Journal of the American Chemical Society, vol. 130, No. 42, Oct. 22, 2008, p. 13969-1397.

Woodyer et al: "Mechanistic investigation of a highly active phosphite dehydrogenase mutant and its application for NADPH regeneration", FEBS Journal, vol. 272, No. 15, Aug. 1, 2005, p. 3816-3827.

(Continued)

*Primary Examiner* — Anand U Desai
(74) *Attorney, Agent, or Firm* — Workman Nydegger

(57) ABSTRACT

A process for the production of furan derivatives from D-glucose, wherein

A) D-glucose is converted into D-fructose in an enzymatic process, wherein redox cofactors are used and regenerated, whereby, as a result of at least two further enzymatically catalyzed redox reactions proceeding in the same reaction batch, one of the two redox cofactors accumulates in its reduced form and, respectively, the other one in its oxidized form, whereby D-glucose is converted into D-fructose, involving two or more oxidoreductases, and B) D-fructose is converted into furan derivatives, and the use of furan derivatives produced in this manner.

29 Claims, 9 Drawing Sheets

(56) References Cited

OTHER PUBLICATIONS

Monti et al: "One-pot Multienzymatic Synthesis of 12-Ketoursodeoxycholic Acid: Subtle Cofactor Specificities Rule the Reaction Equilibria of Five Biocatalysts Working in a Row", Advanced Synthesis and Catalysis, Wiley-VCH Verlag, Weinheim, vol. 351, No. 9, Jun. 1, 2009, p. 1303-1311.

International Preliminary Report on Patentability for PCT Application No. PCT/EP2013/052316 dated Aug. 12, 2014.

Gross, W., Seipold, P., and Schnarrenberger, C. (1997). Characterization and Purification of an Aldose Reductase from the Acidophilic and Thermophilic Red Alga Galdieria sulphuraria. Plant Physiol. 114, 231-236.

Kroutil W., Mang H., Edegger K., and Faber K. (2004). Recent advances in the biocatalytic reduction of ketones and oxidation of sec-alcohols. Current Opinion in Chemical Biology 8, 120-126.

Lee, J., Koo, B., and Kim, S. (2003). Cloning and Characterization of the xyl1 Gene, Encoding an NADH-Preferring Xylose Reductase from Candida parapsilosis, and Its Functional Expression in Candida tropicalis. Applied and Environmental Microbiology 69, 6179-6188.

Mayr, P., Brüggler, K., Kulbe, K., and Nidetzky, B. (2000). d-Xylose metabolism by Candida intermedia:isolation and characterisation of two forms of aldose reductase with different coenzyme specificities. Journal of Chromatography B: Biomedical Sciences and Applications 737, 195-202.

Nidetzky, B., Mayr, P., Neuhauser, W., and Puchberger, M. (2001). Structural and functional properties of aldose xylose reductase from the d-xylose-metabolizing yeast Candida tenuis. Chemico-Biological Interactions 130-132, 583-595.

Old, S., Sato, S., Kador, P., and Carper, D. (1990). In vitro expression of rat lens aldose reductase in *Escherichia coli*. Proceedings of the National Academy of Sciences 87, 4942-4945.

Scheer, B.M., and Horecker, B.L. (1966). Pentose Metabolism in Candida III. The Triphosphopyridine Nucleotide-Specific Polyol Dehydrogenase of Candida utilis. Archives of Biochemistry and Biophysics 116, 117-128.

Schauder, S., Schneider, K.-H., and Giffhorn, F. (1995). Polyol metabolism of Rhodobacter sphaeroides: biochemical characterization of a short chain sorbitol dehydrogenase. Microbiology 141, 1857-1863.

Scott, M., and Viola, R. (1998). The use of fluoro- and deoxy-substrate analogs to examine binding specificity and catalysis in the enzymes of the sorbitol pathway. Carbohydrate Research 313, 247-253.

Uwajima, T. (1999). Purification and properties of NAD+-dependent sorbitol dehydrogenase from Bacillus fructosus. Biosci. Biotechnol. Biochem. 63, 573-574.

Van der Donk, W.A., and Zhao, H. (2003). Recent developments in pyridine nucleotide regeneration. Current Opinion in Biotechnology 14, 421-426.

Vongsuvanlert, V., and Tani, Y. (2006). Characterization of D-Sorbitol Dehydrogenase Involved in D-Sorbitol Production of a Methanol Yeast, Candida boidinii (*Kloeckera* sp.) No. 2201. Agricultural and Biological Chemistry 52, 419-426.

Woodyer, R., Simurdiak, M., Donk, W., and Zhao, H. (2005). Heterologous Expression, Purification, and Characterization of a Highly Active Xylose Reductase from Neurospora crassa. Applied and Environmental Microbiology 71, 1642-1647.

PROCESS FOR THE PRODUCTION OF FURAN DERIVATIVES FROM GLUCOSE

The present invention relates to a process for the production of furan derivatives from D-glucose.

Because of rising costs for fossil raw materials and a diminishing supply of such raw materials, which is to be expected, great interest exists in the utilization of renewable raw materials. In this connection, the fields of energy production and the production of basic chemicals should be differentiated. The present invention refers to the latter field and concerns a process for the production of furan derivatives from D-glucose.

D-Glucose is provided in large amounts in various biopolymers, which are components of renewable raw materials. Examples thereof are starch (e.g., corn starch) or cellulose (e.g., from a lignocellulosic biomass). However, fructose is far better suited as a starting material for the production of furan derivatives.

An established way of converting D-glucose into D-fructose is effected by using a suitable D-glucose isomerase, e.g., D-xylose isomerase, which accepts D-glucose as a substrate. Such methods have already been known for a long time, for example, from U.S. Pat. No. 2,950,228 and are suitable also for industrial use, as described, for instance, in U.S. Pat. No. 3,616,221 or U.S. Pat. No. 3,868,304.

A problem associated therewith is that, usually, a maximum amount of approx 42% of the D-glucose can be converted into D-fructose. A further enrichment of D-fructose relative to D-glucose may be obtained by separation methods. A possibility for this is the application of chromatographic methods, as described, e.g., in U.S. Pat. No. 5,221,478. For the food sector, merely a partial enrichment of D-fructose is thereby often attempted. However, chromatographic methods are very complex especially for the production of a D-fructose which is relatively pure or even highly pure.

Besides the use of isomerases, enzymatic redox reactions on carbohydrates have also been described in the literature.

For example, in DE69839381, a sorbitol dehydrogenase is described which may be used for the conversion of D-sorbitol into L-sorbose and may be applied for the production of ascorbic acid.

In DE10247147, a method is described, wherein D-fructose is reduced to D-mannitol, using D-mannitol-2-dehydrogenase.

In U.S. Pat. No. 4,467,033, the enzymatic oxidation of L-sorbitol into L-fructose is described.

Examples of the reduction of D-xylose into xylitol are disclosed, for example, in US20060035353 or in Woodyer R. et al., FEBS J., 2005, Volume 272, p 3816-3827.

It has already been shown that suitable xylose reductases may be used for reducing D-glucose to D-sorbitol (e.g., Wang X. et al., Biotechnol. Lett., 2007, Volume 29, p 1409-1412).

Sugar redox enzymes such as, e.g., sorbitol dehydrogenase are also used for diagnostic purposes (e.g., DE60006330).

Those methods are individual redox reactions, wherein either a reduction or an oxidation, respectively, occurs for the formation of a product.

Enzymatically catalyzed redox reactions are used in industrial processes, for example, in the production of chiral alcohols, α-amino acids and α-hydroxy acids. Industrial processes as hitherto known usually use a redox enzyme for the synthesis of the product, as well as, optionally, a further enzyme for cofactor regeneration. Processes wherein two or more enzymatic redox reactions which are involved in the formation of the product as well as the optionally required enzymatic reactions for the cofactor regeneration are performed (simultaneously or sequentially) in one reaction batch without an intermediate being isolated must be distinguished therefrom. Recently, such enzymatic cascade reactions—herein referred to as one-pot reactions—have drawn significant attention, since they effectively reduce operating costs, operating time and environmental impacts. In addition, enzymatic cascades of redox reactions facilitate transformations which are not easy to implement by conventional chemical methods.

For example, an attempt to perform the deracemization of racemates of secondary alcohols via a prochiral ketone as an intermediate using a one-pot system has been described (J. Am. Chem. Soc., 2008, Volume 130, p. 13969-13972). The deracemization of secondary alcohols was achieved via two alcohol dehydrogenases (S- and R-specific) with different cofactor specificities. A drawback of the process is the very low concentration of the substrate used of 0.2-0.5%, which is inappropriate for industrial purposes.

A further one-pot system has been described in WO 2009/121785, wherein a stereoisomer of an optically active secondary alcohol was oxidized to the ketone and then reduced to the corresponding optical antipode and wherein two alcohol dehydrogenases having opposite stereoselectivities and different cofactor specificities were used. The cofactors were regenerated by means of a so-called "hydride-transfer system", using only one additional enzyme. For regenerating the cofactors, various enzymes such as formate dehydrogenase, glucose dehydrogenase, lactate dehydrogenase were used. A drawback of said method is the low concentration of the substrates used.

In contrast to that, many individual enzymatic redox reactions are already known. An example of use is the production of chiral hydroxy compounds, starting from appropriate prochiral keto compounds. In said methods, the cofactor is regnerated by means of an additional enzyme. Those methods have in common that they constitute an isolated reduction reaction and regenerate NAD(P)H (see, e.g., EP1152054).

Further examples of an enzymatic production of chiral enantiomerically enriched organic compounds, e.g., alcohols or amino acids, have been described (Organic Letters, 2003, Volume 5, p. 3649-3650; U.S. Pat. No. 7,163,815; Biochem. Eng. J., 2008, Volume 39(2) p. 319-327; EP1285962). In said systems, an NAD(P)H-dependent oxidase from *Lactobacillus brevis* or *Lactobacillus sanfrancisensis* was used as the cofactor regeneration enzyme. The trials likewise constitute single reactions for the formation of a product.

The above-mentioned individually proceeding oxidation or reduction reactions lack the advantages of a one-pot reaction, such as, for example, cost-effectiveness as a result of time and material savings.

An isolation of fructose from aqueous solutions is possible, for example, according to a method described in U.S. Pat. No. 4,895,601 or U.S. Pat. No. 5,047,088.

Various examples of the production of furan derivatives from carbohydrates are known from literature.

In such methods, a plurality of acidic catalysts was used: inorganic acids (see, e.g., Chheda, J. N.; Roman-Leshkow, Y.; Dumesic, J. A. Green Chem. 2007, 9, 342-350), organic acids (e.g., oxalic acid), zeolites (h-form), transition metal ions (see, e.g., Young, G.; Zhang, Y.; Ying, J. Y. Angew. Chem. Int. Ed. 2008, 47, 9345-9348; Tyrlik, S. K.; Szerszen, D.; Olejnik, M.; Danikiewicz, W. Carbohydr. Res. 1999, 315, 268-272), heterogeneously dissolved metal phosphates (see, e.g., Asghari, F. S.; Yoshida, H. Carbohydr. Res. 2006, 341, 2379-2387) or also highly acidic cation exchangers (see, e.g., Villard, R.; Robert, F.; Blank, I.; Bernardinelli, G.; Soldo, T.; Hofmann, T. J. Agric. Food Chem. 2003, 51, 4040-4045).

Water, as a green solvent, was examined preferably as a solvent in such processes. Although a system of a biomass and water may be evaluated as a "green approach", it can no longer be regarded as that at temperatures of >300° C. and pressures of more than 20 MPa, which are required for achieving acceptable yields (see, e.g., Qi, X.; Watanabe, M.; Aida, T. M.; Smith Jr., R. S. Cat. Commun. 2008, 9, 2244-2249).

Hydroxymethylfurfural (in the following HMF) constitutes a special furan compound which may be produced from carbohydrates in the presence of acidic catalysts. Processes for the production of HMF are also known from literature. HMF can be obtained from carbohydrates in an aqueous solution in the presence of homogeneous and heterogeneous acids. Depending on the carbohydrate substrate and the reaction conditions, the obtained yields thereby amount to between 30 and 60%. If water is used as the sovent, reaction conditions of 300° C. and 27 MPa are described also in that case. In addition, the formation of byproducts such as levulinic acid (LS) or insoluble humic acids is described (see, e.g., Bicker, M., Kaiser, D., Ott, L., Vogel, H., J. of Supercrit. Fluids 2005, 36, 118-126; Szmant, H. H., Chundury, D. D., J. Chem. Techn. Biotechnol. 1981, 31, 135-145; Srokol, Z., Bouche, A.-G., van Estrik, A., Strik, R. C. J., Maschmeyer, T., Peters, J. A., Carbohydr. Res. 2004, 339, 1717-1726).

A flow process under supercritical conditions, starting from D-glucose, has been described by Aida et al. (Aida, T. A.; Sato, Y.; Watanabe, M.; Tajima, K.; Nonaka, T.; Hattori, H.; Arai, K. J. of Supercrit. Fluids, 2007, 40, 381-388).

Organic solvents might also be suitable for HMF production. However, a significant limitation thereof is that, in some cases, they are hard to separate from the product (see, e.g., Bao, Q.; Qiao, K.; Tomido, D.; Yokoyama, C. Catal. Commun. 2008, 9, 1383-1388; Halliday, G. A.; Young Jr., R. J.; Grushin, V. V. Org. Lett. 2003, 5, 2003-2005). In addition, many solvents which were used in the past are not suitable for possibly subsequent reactions, but produce byproducts, unless they are separated. Solvents which are frequently used for the conversion of carbohydrates into HMF are dimethyl sulfoxide (DMSO) and dimethyl formamide (DMF). Compared to water as a solvent, the conversions of carbohydrates into HMF can be performed in those cases already at comparatively low temperatures of 80-140° C. and produce significantly higher yields (up to 95% in DMF) within shorter reaction times (30 min to 2 h) (see, e.g., Halliday, G. A., Young Jr., R. J., Grushin, V. V., Org. Lett. 2003, 5, 2003-2005; WO2009076627. It is assumed that DMSO acts as a catalyst in the dehydration of D-fructose (or of other carbohydrates) into HMF (and comparable compounds) (see: Amarasekara, A. S.; Williams, L. D.; Ebede, C. C. Carbohydr. Res. 2008, 343, 3021-3024).

Reaction mixtures of water/DMSO or water/toluene were also used in a continuous reaction regime, wherein reaction times of 4-6 h at 140-180° C. were required in order to obtain an HMF yield of, at best, 80% (see Chheda, J. N., Roman-Leshkov, Y., Dumesic, J. A., Green Chem. 2007, 9, 342-350).

Ionic liquids may act both as neutral solvents and as active Brønsted acids, wherein the separation of the ionic liquids continues to be a problem. In addition, immobilized ionic liquids were used as Brønsted-acid catalysts (see Bao, Q.; Qiao, K.; Tomido, D.; Yokoyama, C. Catal. Commun. 2008, 9, 1383-1388).

All processes known to date display various drawbacks, for example, a low initial concentration of the substrate, low total yields.

Surprisingly, a possibility of achieving a better total yield during the production of furan derivatives from D-glucose has now been found, wherein surprisingly high initial concentrations of D-glucose may be used.

In one aspect, the present invention provides a process for the production of furan derivatives from D-glucose, which is characterized in that A) D-glucose is converted into D-fructose in an enzymatic process, wherein redox cofactors are used and regenerated, whereby, as a result of at least two further enzymatically catalyzed redox reactions proceeding in the same reaction batch, one of the two redox cofactors accumulates in its reduced form and, respectively, the other one in its oxidized form, whereby D-glucose is converted into D-fructose, involving two or more oxidoreductases, and B) D-fructose is converted into furan derivatives.

A process provided by the present invention is referred to herein also as the process according to/of the present invention.

A particular embodiment of the present invention is characterized in that NAD⁺/NADH and/or NADP⁺/NADPH are used as redox cofactors in Step A).

In a further aspect, the present invention provides a process for the production of furan derivatives from D-glucose, which is characterized in that, in Step A) D-glucose is converted into D-fructose in an enzymatic process, wherein the redox factors NAD⁺/NADH and/or NADP⁺/NADPH are used and regenerated, whereby, as a result of at least two further enzymatically catalyzed redox reactions (product-forming reactions) proceeding in the same reaction batch, one of the two redox cofactors accumulates in its reduced form and, respectively, the other one in its oxidized form, wherein in the regeneration reaction reconverting the reduced cofactor into its original oxidized form, oxygen or a compound of general formula

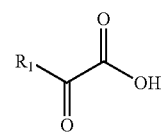

wherein $R_1$ represents a linear-chain or branched $(C_1-C_4)$-alkyl group or a $(C_1-C_4)$-carboxyalkyl group, is reduced, and in the regeneration reaction reconverting the oxidized cofactor into its original reduced form, a $(C_4-C_8)$-cycloalkanol or a compound of general formula

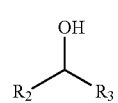

wherein $R_2$ and $R_3$ are independently selected from the group consisting of H, $(C_1-C_6)$-alkyl, wherein alkyl is linear-chain or branched, $(C_1-C_6)$-alkenyl, wherein alkenyl is linear-chain or branched and contains one to three double bonds, aryl, in particular $C_6-C_{12}$-aryl, carboxyl, or $(C_1-C_4)$-carboxyalkyl, in particular also cycloalkyl, e.g., $C_3-C_8$-cycloalkyl, is oxidized.

In a further aspect, in a process according to the present invention, $R_1$ is a substituted or unsubstituted, e.g., an unsubstituted C1-C4-alkyl group.

In a further aspect, in a process according to the present invention, $R_2$ and $R_3$ are independently selected from the group consisting of H, $(C_1-C_6)$-alkyl, wherein alkyl is linear-chain or branched, $(C_1-C_6)$-alkenyl, wherein alkenyl is linear-chain or branched and contains one to three double bonds, aryl, in particular $C_6-C_{12}$-aryl, carboxyl, or $(C_1-C_4)$-carboxyalkyl.

In a process according to the present invention enzymatically catalyzed redox reactions which are not part of the cofactor regeneration and which are involved in the formation of the product are herein referred to as "oxidation reaction(s)" and "reduction reaction(s)". "Oxidation reaction(s)" and "reduction reaction(s)" are summarized under the term "product-forming reactions". The product-forming reactions in a process according to the present invention comprise, in each case, at least one oxidation reaction and at least one reduction reaction.

In a preferred embodiment of the present invention, a process according to the present invention is characterized in that oxidation reaction and reduction reaction proceed chronologically parallel.

Enzymes and redox enzymes in a process according to the present invention include oxidoreductases. Oxidoreductases are enzymes which catalyze redox reactions. Oxidoreductases include, for example, dehydrogenases, reductases, oxidases, catalases. The indication of an acid or a salt of an acid includes herein the respective non-indicated term. Likewise, the indication of acids, in particular of bile acids, includes herein all esters derived therefrom. Furthermore, compounds (partly) provided with protective groups are included where the underlying substances are indicated.

In a preferred embodiment of the present invention, a process according to the present invention is characterized in that, as a compound of formula I (2-oxo acid), pyruvate (redox cosubstrate) is used which is reduced to lactate by means of a lactate dehydrogenase, which means that, in the regeneration reaction reconverting the reduced cofactor into its original oxidized form, pyruvate is reduced to lactate by means of a lactate dehydrogenase.

In a preferred embodiment of the present invention, a process according to the present invention is characterized in that, as a compound of formula II (redox cosubstrate), a secondary alcohol, in particular 2-propanol (isopropyl alcohol, IPA) is used which is oxidized to acetone by means of an alcohol dehydrogenase, which means that, in the regeneration reaction reconverting the oxidized cofactor into its original reduced form, 2-propanol is oxidized to acetone by means of an alcohol dehydrogenase.

In a preferred embodiment of the present invention, a process according to the present invention is characterized in that, as a redox cosubstrate, oxygen is used which is reduced by means of an NADH oxidase.

In a preferred embodiment of the present invention, a process according to the present invention is characterized in that, as a redox cosubstrate, a secondary alcohol malate is used which is oxidized to pyruvate and $CO_2$ by means of an oxaloacetate-decarboxylating malate dehydrogenase ("malate enzyme"), e.g., that, in the regeneration reaction reconverting the oxidized cofactor into its original reduced form, malate is oxidized to pyruvate and $CO_2$ by means of a malate dehydrogenase.

In this embodiment, the nascent pyruvate is reacted in a further redox reaction which does not serve for the formation of a product, but constitutes the second cofactor regeneration reaction. Appropriate sources of D-glucose in a process according to the present invention include, for example, enzymatic or non-enzymatic hydrolysates of starch, in particular corn starch, enzymatic or non-enzymatic hydrolysates of saccharose or enzymatic or non-enzymatic hydrolysates of cellulose. Cellulose used in a process according to the present invention may be obtained, for example, from a biomass, preferably from a lignocellulosic biomass such as, e.g, wood, straw such as wheat straw, corn straw, bagasse, sisal, energy grasses. For example, amylases may be used for the enzymatic hydrolysis of corn starch. For example, invertases are suitable for the enzymatic cleavage of saccharose. For example, cellulases may be used for the enzymatic cleavage of cellulose. An acid-catalyzed cleavage, for example, is suitable for the non-enzymatic cleavage of said multiple sugars.

Step A) in a process according to the present invention is performed in an aqueous system to which a buffer is optionally added. Suitable buffers include, for example, acetate, potassium phosphate, Tris-HCl and glycine buffers, which have, for example, a pH-value of from 5 to 10.5, preferably from 6 to 10. Furthermore or alternatively, ions for stabilizing the enzymes, such as, e.g., $Mg^{2+}$ or other additives such as, for example, glycerol, may be added to the system during the conversion of D-glucose into D-fructose.

In a process according to the present invention, in Step A), D-glucose is converted into D-fructose according to Reaction Scheme 1

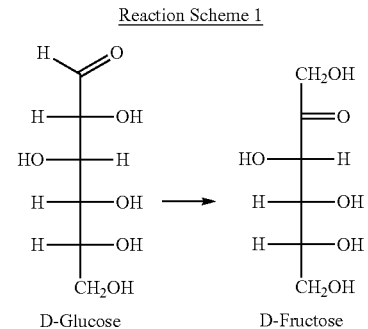 [SMILES: O=CC(O)C(O)C(O)C(O)CO ; O=C(CO)C(O)C(O)C(O)CO]

Reaction Scheme 1

D-Glucose → D-Fructose

In a further aspect, the present invention is characterized in that, during the conversion of D-glucose into D-fructose, at first an enzymatically catalyzed reduction and subsequently an enzymatically catalyzed oxidation are performed.

In a specific aspect, the present invention is characterized in that isomerization of D-glucose occurs via reduction to D-sorbitol, which is oxidized into D-fructose, in particular according to the following Reaction Scheme 2

Reaction Scheme 2

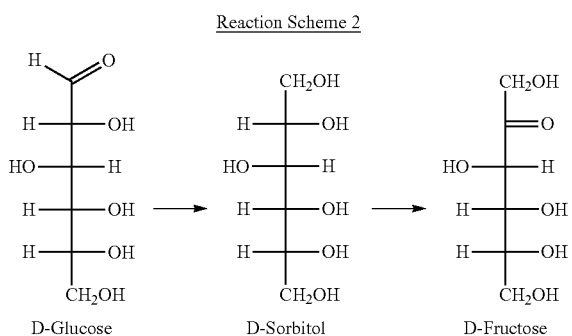 [SMILES: O=CC(O)C(O)C(O)C(O)CO ; OCC(O)C(O)C(O)C(O)CO ; O=C(CO)C(O)C(O)C(O)CO]

A further specific embodiment of the process according to the present invention is characterized in that both the reduction and the oxidation reaction(s) for converting D-glucose into D-fructose occur in the same reaction batch, without any intermediates being isolated.

Appropriate enzymes for the reduction of D-glucose into D-sorbitol are known and include, for example, xylose reductases which can be obtained, for instance, from *Candida tropicalis* or *Candida parapsilosis*.

Appropriate enzymes for the oxidation of D-sorbitol into D-fructose are known and include, for example, sorbitol dehydrogenases which can be obtained, for instance, from sheep liver, *Bacillus subtilis* or *Malus domestica*.

A particular embodiment of the process according to the present invention is characterized in that at least one dehydrogenase as well as redox cofactor(s), e.g. the redox cofactor(s) $NAD^+/NADH$ and/or $NADP^+/NADPH$, are used for the conversion of D-glucose into D-fructose.

Both the enzymes and the redox cofactors may thereby be used either in a soluble form or immobilized onto a carrier (solid).

A further specific embodiment of the process according to the present invention is characterized in that the redox cofactor(s) $NAD^+/NADH$ and/or $NADP^+/NADPH$ are regenerated by at least one further redox enzyme (reconverted into their original redox state).

Redox enzymes which are suitable for regenerating $NAD^+/NADH$ and/or $NADP^+/NADPH$ are known and familiar to a person skilled in the art and include, for example, dehydrogenases.

In a process according to the present invention, both individual enzymes and fusion proteins comprising two redox enzymes may be used in Step A).

A further specific embodiment of the process according to the present invention is characterized in that enzymatic redox reactions for converting D-glucose into D-fructose are catalyzed by such dehydrogenases which are using the redox cofactors $NAD^+/NADH$ and/or $NADP^+/NADPH$.

Therein, $NAD^+$ denotes the oxidized form and NADH denotes the reduced form of nicotinamide adenine dinucleotide, whereas $NADP^+$ denotes the oxidized form and NADPH denotes the reduced form of nicotinamide adenine dinucleotide phosphate. Adding redox cofactors is possibly unnecessary if the enzyme solutions already contain them at sufficient concentrations. If the redox cofactors $NAD(P)^+$ and/or NAD(P)H are added during the conversion of D-glucose into D-fructose, the added concentration in a process according to the present invention usually ranges from 0.001 mM to 10 mM, preferably from 0.01 mM to 1 mM.

Preferably, the used redox cofactors are regenerated in the same reaction batch by at least one further redox enzyme during the conversion of D-glucose into D-fructose, with cosubstrates being consumed.

A further specific embodiment of the process according to the present invention is characterized in that at least one redox cofactor is regenerated in the same reaction batch by at least one further redox enzyme during the conversion of D-glucose into D-fructose, with cosubstrates being consumed.

Further redox enzymes for regenerating the redox factors are known to a person skilled in the art and include, for example, alcohol dehydrogenases, NADH oxidases, hydrogenases, lactate dehydrogenases or formate dehydrogenases.

A further specific embodiment of the process according to the present invention is characterized in that $NAD^+$ is regenerated in the same reaction batch by an NADH oxidase during the conversion of D-glucose into D-fructose.

A further specific embodiment of the process according to the present invention is characterized in that NADPH is regenerated in the same reaction batch by an alcohol dehydrogenase during the conversion of D-glucose into D-fructose.

NADH oxidases and alcohol dehydrogenases are known to a person skilled in the art. Alcohol dehydrogenases include, for example, those from *Lactobacillus* kefir. Suitable NADH oxidases are obtainable, for example, from *Leuconostoc mesenteroides*, *Streptococcus mutans*, *Clostridium aminovalericum*.

A further specific embodiment of the process according to the present invention is characterized in that NADPH is regenerated in the same reaction batch by the alcohol dehydrogenase from *Lactobacillus* kefir during the conversion of D-glucose into D-fructose.

For regenerating the redox enzymes, cosubstrates must be provided and optionally added.

Substances which are reduced or oxidized during the regeneration of $NAD^+/NADH$ and/or $NADP^+/NADPH$ (or of other redox cofactors) are referred to as cosubstrates. Appropriate cosubstrates in a process according to the present invention include, for example, alcohols (e.g., 2-propanol), lactic acid and salts thereof, pyruvic acid and salts thereof, oxygen, hydrogen and/or formic acid and salts thereof.

NADPH may be regenerated, for example, by the alcohol dehydrogenase from *Lactobacillus* kefir, adding the cosubstrate 2-propanol (isopropanol), which is oxidized into acetone.

Possible reaction pathways for the conversion of D-glucose into D-fructose according to a process of the present invention are illustrated in the subsequent Reaction Schemes 3 and 4:

Reaction Scheme 3

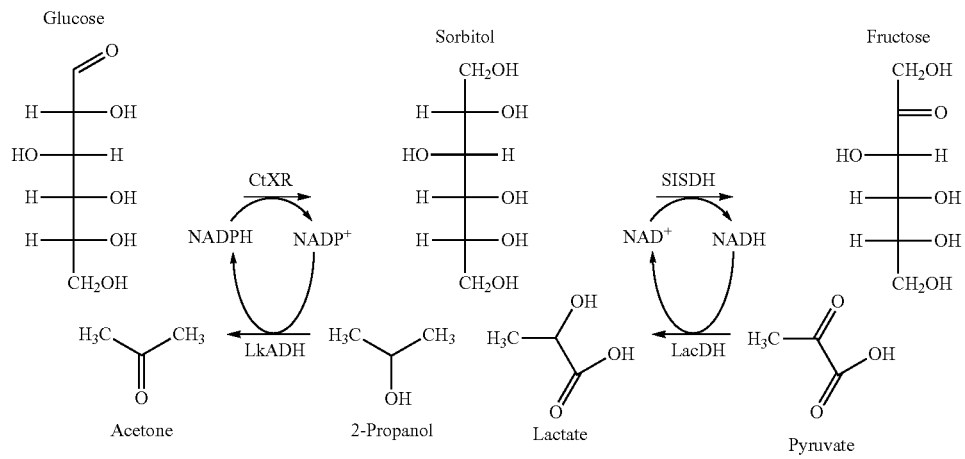

CtXR = xylose reductase from *Candida tropicalis*
SlSDH = sorbitol dehydrogenase from sheep liver
LkADH = alcohol dehydrogenase from *Lactobacillus kefir*, NADP(H)-dependent
LacDH = lactate dehydrogenase, NAD(H)-dependent Reaction Scheme 4

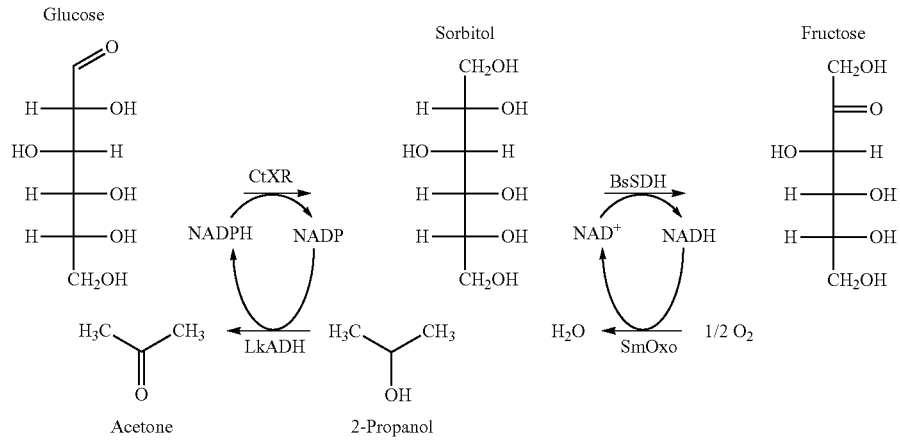

CtXR = xylose reductase from *Candida tropicalis*
BsSDH = sorbitol dehydrogenase from *Bacillus subtilis*
LkADH = alcohol dehydrogenase from *Lactobacillus kefir*, NADP(H)-dependent
SmOxo = NADH oxidase from *Streptococcus mutans*

It has been found that, in a process according to the present invention, a high initial concentration of D-glucose in the aqueous reaction mixture of ≥5% (w/v) D-glucose, preferably ≥10% (w/v) D-glucose, particularly preferably ≥15% (w/v) D-glucose, may be used in the conversion of D-glucose into D-fructose.

In a further preferred embodiment, the D-glucose is used in the aqueous reaction mixture in a process according to the present invention at a concentration of ≥5% (w/v) D-glucose, preferably ≥10% (w/v) D-glucose, particularly preferably ≥15% (w/v) D-glucose, wherein a concentration of 50% (w/v), preferably 40% (w/v), particularly preferably 35% (w/v), should not be exceeded.

Due to the temperature-dependent solubility of D-glucose, the glucose concentration is to be adjusted to the respective reaction temperature during the implementation of the process.

In a process according to the present invention, enzymes may be used as such, optionally in the form of cell lysates, optionally as recombinantly overexpressed proteins, for example, as proteins recombinantly overexpressed in *E. coli*, wherein, also preferably, the respective cell lysates may be used without any further purification. Depending on the enzyme to be produced, other microorganisms may also be used for expression, e.g., microorganisms known to the skilled artisan. In a process according to the present invention, solid components of the respective microorganisms can either be separated or used in the reaction, too (e.g., wholecell biocatalysts). Culture supernatants or lysates from microorganisms which already display sufficient enzyme activities without recombinant DNA technology may also be used. In a process according to the present invention, both enzymes and redox cofactors may be used either in a soluble form or immobilized onto solids. Thereby, the enzyme unit 1 U corresponds to the enzyme amount which is required for reacting 1 µmol of substrate per min.

Surprisingly, it has been found that, in a process according to the present invention, a high turnover can be achieved during the conversion of D-glucose into D-fructose, for example, a turnover of ≥70% (w/v), such as ≥90% (w/v), e.g., ≥98% (w/v) and up to 99.9% (w/v), or even a complete turnover.

Depending on the enzymes used, the process according to the present invention can be performed, for example, in Step A) at temperatures ranging from 10° C. to 70° C., preferably at room temperature, e.g., 20° C., up to 50° C.

The D-fructose which can be obtained according to Step A) of the present invention may be isolated, e.g., by means of crystallization.

The 50% D-glucose proportion accumulating, for example, during the cleavage of saccharose may be converted into D-fructose by means of a two-step enzymatic redox process according to the present invention, resulting in an increase in the proportion of D-fructose in the overall sugar content. Therewith, a suitable starting material for a further conversion into furan derivatives is accessible, wherein it has surprisingly been found that the intermediate D-fructose, which is obtained according to a process of the present invention, may be used particularly well for a further conversion into furan derivatives.

The conversion of D-fructose into furan derivatives in Step B) according to the present invention may occur according to a suitable method, e.g., a common method, or as described herein.

According to common methods, the conversion of D-fructose into furan derivatives may occur in a process according to the present invention in the presence of a catalyst, e.g., an acidic catalyst such as an inorganic acid, an organic acid, e.g., oxalic acid, a zeolite (H-form), of transition metal ions, a heterogeneously dissolved metal phosphate, a highly acidic cation exchanger.

Water or an organic solvent, e.g., dimethyl sulfoxide (DMSO), dimethyl formamide (DMF), N-methylpyrrolidone, may be used as a solvent in such processes.

The conversion of D-fructose into furan derivatives in Step B) preferably occurs according to the present invention in the presence of an acidic catalyst and in the presence of N-methylpyrrolidone (N-methyl-2-pyrrolidone, NMP) of formula

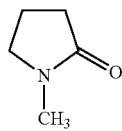

The conversion of D-fructose into furan derivatives in Step B) according to the present invention may either be performed as a batch process or as a continuous process.

In a preferred embodiment, Step B) is performed according to the present invention under microwave heating.

Particular embodiments of the process according to the present invention are characterized in that, during the conversion of D-fructose into furan derivatives, N-methyl-2-pyrrolidone (NMP) is used either as a reaction solvent or as a co-solvent, namely as an admixture to another solvent.

In a particular embodiment of a process according to the present invention, NMP is used in Step B) as a (co)-solvent, e.g., as a reaction solvent or as an admixture to another solvent.

In a process according to the present invention, when NMP is being used as a solvent, NMP may be used as the only solvent, or NMP is used together with a co-solvent, wherein an NMP concentration of up to 70% (v/v), for example, up to 60% (v/v), based on the total amount of solvent, may be used in the event of the use of a co-solvent. For example, water or organic solvents, e.g., such as known from the prior art, e.g. N,N-dimethyl sulfoxide (DMSO) or N,N-dimethyl formamide (DMF), may be considered as co-solvents.

In a process according to Step B) of the present invention, D-fructose may be used in an amount of up to 40% (w/v) and generally is used in an amount of from 5 to 20%, although the reaction proceeds also at a lower concentration, for example, at a D-fructose concentration of (about) 1% (w/v). The minimum value is thereby defined by cost-effectiveness rather than chemically.

Acidic catalysts in Step B) in a process according to the present invention include common acidic catalysts which may be used for the conversion of fructose into furan derivatives. Preferably, the catalyst is a Brønsted acid. Homogeneous acid catalysts, e.g., sulphuric acid or hydrochloric acid, or heterogeneous acid catalysts, for example, cation-exchange resins such as montmorillonites, preferably Montmorillonite KSF®, or amberlites, e.g., Amberlite®, preferably Amberlite 15®, may thereby be used. In addition, Lewis acid catalysts such as $CrCl_2$, $AlCl_3$, $SiO_2$—$MgCl_2$ or an SILP (silica supported ionic liquid phase) catalyst may be used in a process according to the present invention. Generally, however, they do not provide results as good as those of the above-mentioned catalysts.

In a further aspect, a process according to the present invention is characterized in that
 a homogeneous acid catalyst, preferably sulphuric acid or hydrochloric acid;
 a heterogeneous acid catalyst, preferably an ion exchanger, e.g., a montmorillonite such as Montmorillonite KSF® or an amberlite such as Amberlite®, preferably Amberlite 15®,
 a Lewis acid catalyst such as, e.g., $CrCl_2$, $AlCl_3$ or $SiO_2$—$MgCl_2$,
 an SILP catalyst,
 preferably a homogeneous or heterogeneous acid catalyst, is used as the acidic catalyst during the conversion of D-fructose into furan derivatives in Step B).

A person skilled in the art can easily ascertain the amount of a catalyst required in Step B) by simple preliminary tests. The amount thereby depends on the type of the catalyst which is used.

In the following, catalyst amounts, based on the amount of fructose used are indicated by way of example, particularly for the case of NMP being used as a solvent:

| Catalyst | amount |
| --- | --- |
| 1N HCl | 20 to 200% (v/w) |
| HCl (37%) | 2 to 25% (v/w) |
| 1N $H_2SO_4$ | 20 to 200% (v/w) |
| $H_2SO_4$ conc | 2 to 25% (v/w) |

-continued

| Catalyst | amount |
|---|---|
| Montmorillonite KSF ® | 1 to 50% (w/w) |
| Amberlite 15 ® | 1 to 50% (w/w) |
| CrCl$_2$, AlCl$_3$ | 1 to 20% (w/w) |
| SiO$_2$—MgCl$_2$ | 20 to 200% (w/w) |
| SILP | 10-200% (w/w) |

Therein, the indicated values are unproblematic at a concentration of about 10% (w/v) D-fructose, at higher fructose concentrations, the amount of catalysts has to be restricted such that the fructose can still be dissolved in the remaining amount of solvent.

The process in Step B) according to the present invention is performed at appropriate temperatures. Appropriate temperatures include temperatures from 100 to 220° C., preferably from 115 to 200° C., particularly preferably from 135 to 185° C., especially when NMP is being used as a solvent.

The reactions in Step B), using NMP as a solvent, were experimentally conducted continuously in closed vessels (batch, microwave), without active pressure control. From the microwave passages, approx. 2-4 bar can be determined as the maximum pressure with NMP, which depends strongly on the additives. If, for example, HCl is used as the catalyst, the nascent pressure rises as far as to 15 bar. In a continuous operation, a constant back pressure of up to about 40 bar was applied in order to avoid boiling of the solvent. Pressure is generated either as a vapour pressure of (a) solvent(s) or additives, or a systemic (pump) pressure is applied. However, for the reaction mechanism, the pressure does not appear to be decisive.

It has turned out that, in a process according to the present invention, the furan derivative forming primarily is hydroxymethylfurfural (HMF) of formula

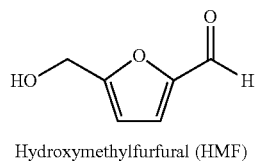

Hydroxymethylfurfural (HMF)

In a further aspect, a process according to the present invention is characterized in that the furan derivative is hydroxymethylfurfural.

In a process according to the present invention, the proportion of spent D-fructose which is converted into HMF is to be understood as "HMF" selectivity.

Furan derivatives which are produced by a process according to the present invention either can be used directly or can be converted into secondary products in further chemical reactions. For example, hydroxymethylfurfural can be oxidized further into 2,5-furan dicarboxylic acid (FDCA) of formula

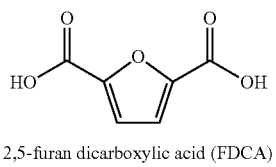 [SMILES: O=C(O)c1ccc(C(=O)O)o1]

2,5-furan dicarboxylic acid (FDCA)

FDCA is known to be suitable as a monomer for the production of polymers such as, e.g., polyethylene furanoate (PEF), which can be used similarly as polyethylene terephthalate (PET), for example for hollow bodies, in particular bottles such as, e.g., beverage bottles, bottles for cosmetics or bottles for cleaning agents. When ethylene glycol from regenerative sources and FDCA, which is accessible from HMF, produced in a process according to the present invention, are used simultaneously, a PEF consisting virtually completely of renewable raw materials may be obtained.

In a further aspect, the present invention is characterized in that furan derivatives which are produced are converted further, for example, that hydroxymethylfurfural is oxidized further into 2,5-furan dicarboxylic acid, which, optionally, is subjected to polymerization, for example, for the production of polymers such as, e.g., polyethylene furanoate (PEF).

Example 1

Figure 1:
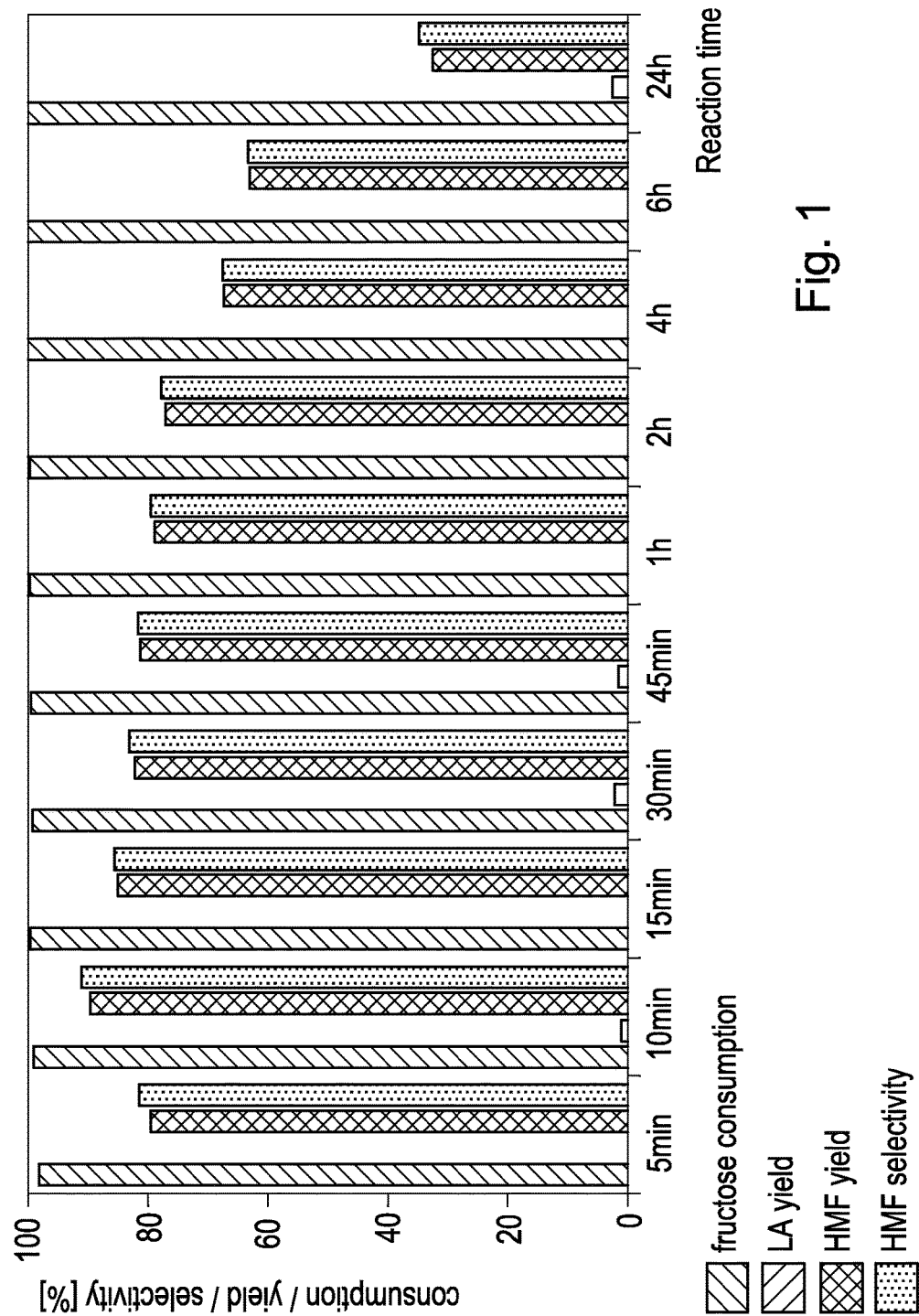
FIG. 1
shows results in the dehydration of D-fructose in N-methyl-2-pyrrolidone, with sulphuric acid as a catalyst, according to Example 5

Conversion of D-Glucose into D-Fructose Via a Xylose Reductase and a Sorbitol Dehydrogenase, Using an Alcohol Dehydrogenase for Recycling the NADPH and a Lactate Dehydrogenase for Recycling the NAD+

A 0.5 ml batch contains 50 mg/ml D-glucose and 6 U/ml of recombinant xylose reductase from *Candida tropicalis* (overexpressed in *E. coli* BL21 (DE3)) and 0.1 mM NADP+. For the regeneration of the cofactor, 7% (v/v) IPA and 6 U/ml of recombinant alcohol dehydrogenase from *Lactobacillus kefir* (overexpressed in *E. coli* BL21 (DE3)) are added. The enzymes are used in the form of cell lysates. The reaction takes place for 24 h at 40° C. and pH=9 (50 mM Tris HCl-buffer) in an open system, with continuous shaking (900 rpm). The open system leads to the removal of the acetone formed, which drives the reaction toward the formation of D-sorbitol. In the open system, water and IPA evaporate too, so that they are additionally dosed in after 6 h and after 21 h. Thereby, at each time, a total volume of 0.5 ml as well as an IPA concentration of 7% (v/v) are again adjusted. After 24 h, the reaction vessel is incubated at 60° C. under vacuum in order to inactivate the enzymes and to evaporate the organic solvents. After cooling to RT, the recombinant D-sorbitol dehydrogenase from *Bacillus subtilis* (overexpressed in *E. coli* BL21 (DE3)) is added at a final concentration of 5 U/ml, ZnCl$_2$ at a final concentration of 1 mM and NAD+ at a final concentration of 0.1 mM. For cofactor regeneration, 5 U/ml (final concentration) of lactate dehydrogenase from rabbit muscles (Sigma Aldrich) and 300 mM pyruvate are used. The batch is topped up to 0.5 ml with water. The reaction takes place for further 24 h at 40° C. in a closed system with continuous shaking (900 rpm). A conversion of D-glucose into D-fructose of >90% is achieved.

Example 2

Conversion of D-Glucose into D-Fructose Via a Xylose Reductase and a Sorbitol Dehydrogenase, Using an Alcohol Dehydrogenase for Recycling the NADPH and an Oxidase for Recycling the NAD+

A 0.5 ml batch contains 50 mg/ml D-glucose, 6 U/ml of recombinant xylose reductase from *Candida tropicalis* (overexpressed in *E. coli* BL21 (DE3)) and 0.1 mM NADP+. For the regeneration of the cofactor, 7% (v/v) IPA and 6 U/ml of recombinant alcohol dehydrogenase from *Lactobacillus* kefir (overexpressed in *E. coli* BL21 (DE3)) are added. The enzymes are used in the form of cell lysates. The reaction takes place for 24 h at 40° C. and pH=8 (50 mM Tris HCl buffer) in an open system, with continuous shaking (900 rpm). The open system leads to the removal of the nascent acetone, which drives the reaction toward the formation of D-sorbitol. In the open system, water and IPA evaporate, too, so that they are additionally dosed in after 6 h and after 21 h. Thereby, at each time, a total volume of 0.5 ml as well as an IPA-concentration of 7% (v/v) are again adjusted. After 24 h, the reaction vessel is incubated at 60° C. under vacuum in order to inactivate the enzymes and to evaporate IPA as well as any acetone that has formed. After cooling to room temperature, the recombinant D-sorbitol dehydrogenase from *Bacillus subtilis* (overexpressed in *E. coli* BL21 (DE3)) is added at a final concentration of 5 U/ml, CaCl$_2$ at a final concentration of 1 mM and a mixture (1:1) of NAD+ and NADH at a final concentration of 0.1 mM. For cofactor regeneration, 10 U/ml (final concentration) of NADH oxidase from *Leuconostoc mesenteroides* (overexpressed in *E. coli* BL21 (DE3)) is used. The enzymes are used in the form of cell lysates. The batch is topped up to 0.5 ml with water. The reaction takes place for another 24 h at 40° C. in an open system, with continuous shaking (900 rpm), in order to ensure sufficient oxygen supply for the NADH oxidase from the air. In that open system at 40° C. water evaporates. Thus, after 6 h and after 21 hit is filled up with water to a volume of 0.5 ml. A conversion of D-glucose into D-fructose of approx. 98% is achieved.

Example 3

Reprocessing and Analytics of Sugars

The batch is incubated at 65° C. for 10 min for inactivating the enzymes and is subsequently centrifuged. The supernatant is then filtered over a 0.2 µM PVDF filter and analyzed by ligand-exchange HPLC (Agilent Technologies Inc.). In doing so, sugars and polyols are separated via a lead column of Showa Denko K.K. (Shodex® Sugar SP0810) with a flow of 0.5 ml/min water (VWR International GmbH, HPLC Grade) at 80° C. Detection occurs with the aid of a light-refraction detector (RID, Agilent 1260 Infinity®, Agilent Technologies Inc.). An inline filter of Agilent Technologies Inc. and, as precolumns, an anion-exchange column (Shodex® Axpak-WAG), a reversed-phase column (Shodex® Asahipak® ODP-50 6E) and a sugar precolumn (SUGAR SP-G), in each case from Showa Denko K.K., are used.

Example 4

Figure 8:
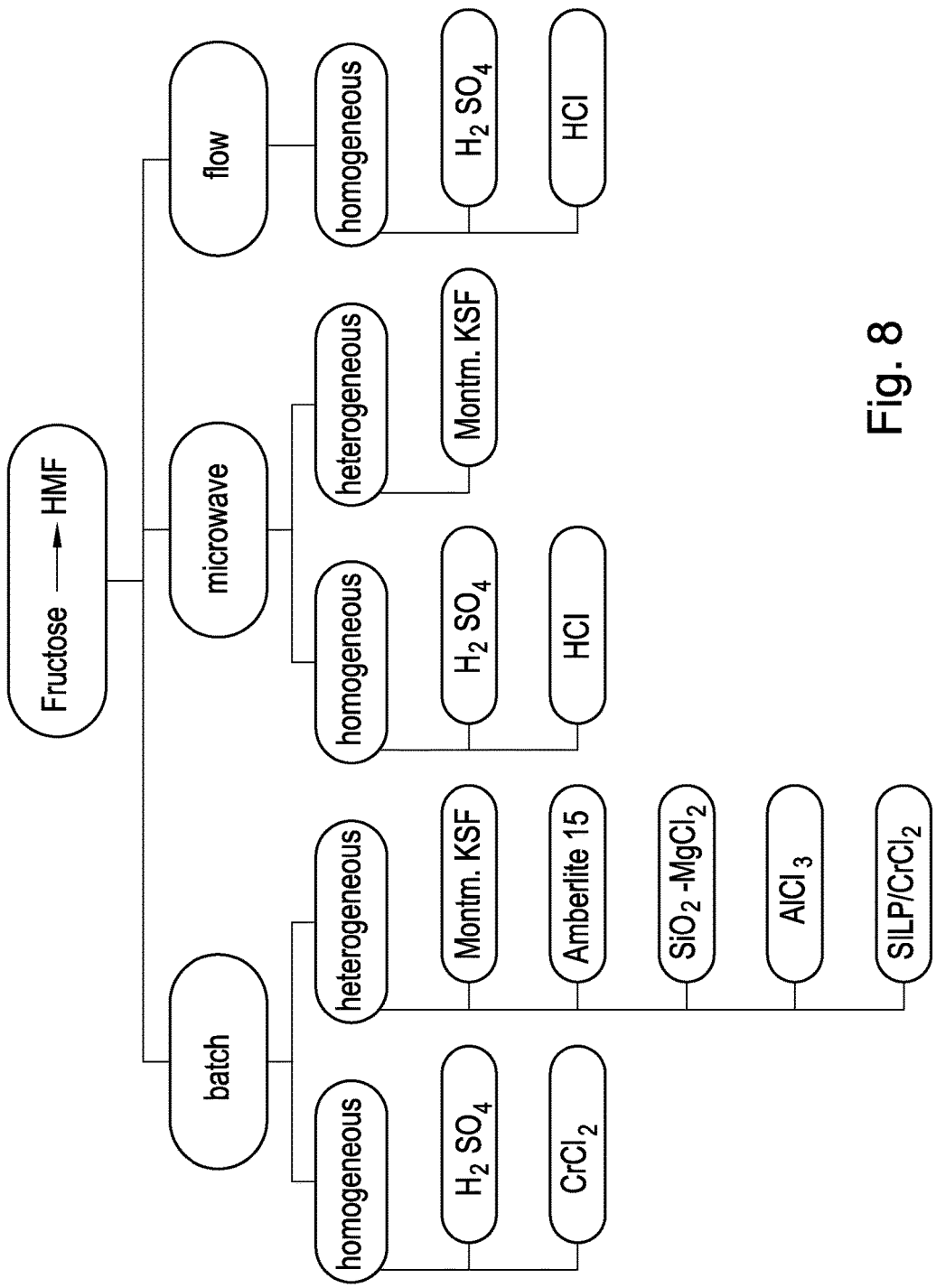
FIG. 8
shows a survey of the tested conditions during the dehydration of D-fructose

Materials and Methods for the Conversion of D-Fructose into Furan Derivatives In the context of this invention, dehydration reactions of D-fructose into HMF were performed under various reaction conditions, optionally as a standard batch process, with microwave-assisted heating or using "continuous flow" conditions. FIG. 8 shows a survey of the tested conditions. Surprisingly, it has been found that NMP as a solvent yields higher turnovers in the reaction compared to hitherto known systems, in combination with homogeneous or heterogeneous catalysts both in the microwave-assisted method and under "continuous flow" conditions.

Synthesis of SiO$_2$—MgCl$_2$

SiO$_2$—MgCl$_2$ was produced according to a provision by Yasuda et al. (Yasuda, M.; Nakamura, Y.; Matsumoto, J.; Yokoi, H. Shiragami, T. Bull. Chem. Soc. Jpn. 2011, 84, 416-418).

Synthesis of SILPs

The SILP catalyst was produced in accordance with known provisions (Fu, S.-K.; Liu, S.-T. Synth. Commun. 2006, 36, 2059-2067) by using N-methyl imidazol. For immobilization, the obtained ionic liquid was mixed with 200% by weight of silica gel in dry chloroform (100 mL pro 10 g SiO$_2$) and heated to 70° C. for 24 h. The obtained solid was filtered off, washed with chloroform and dried under reduced pressure. The silica gel obtained exhibited a load of approx. 16% by weight of a catalyst.

General Conditions Batch Reactions

Unless specified otherwise, all batch reactions were performed in a 4 mL screw lid jar. Heating to the desired temperature was effected in appropriate aluminium blocks.

Microwave Reactions in a Batch Process

In the batch process, microwave reactions were performed on a Biotage-Initiator Sixty laboratory microwave equipped with an autosampler in order to enable sequential reaction regimes. The absorption level was adjusted to a maximum value, whereby the maximum energy supply was automatically set to 400 W.

Stopped Flow Microwave Reactions and Continuous Flow Reactions

Stopped flow reactions for optimizing a semi-continuous process management were performed on a CEM® Discover System with CEM® Voyager Upgrade and by means of an external pressure sensor. For reactions with continuous process management, a cartridge-based reactor system X-Cube from ThalesNano® equipped with a Gilson® GX-271 Autosampler for automatic product gathering was used. Thereby, two quartz sand cartridges (CatCart®, 70×4 mm) were incorporated as a reaction zone.

Figure 9:
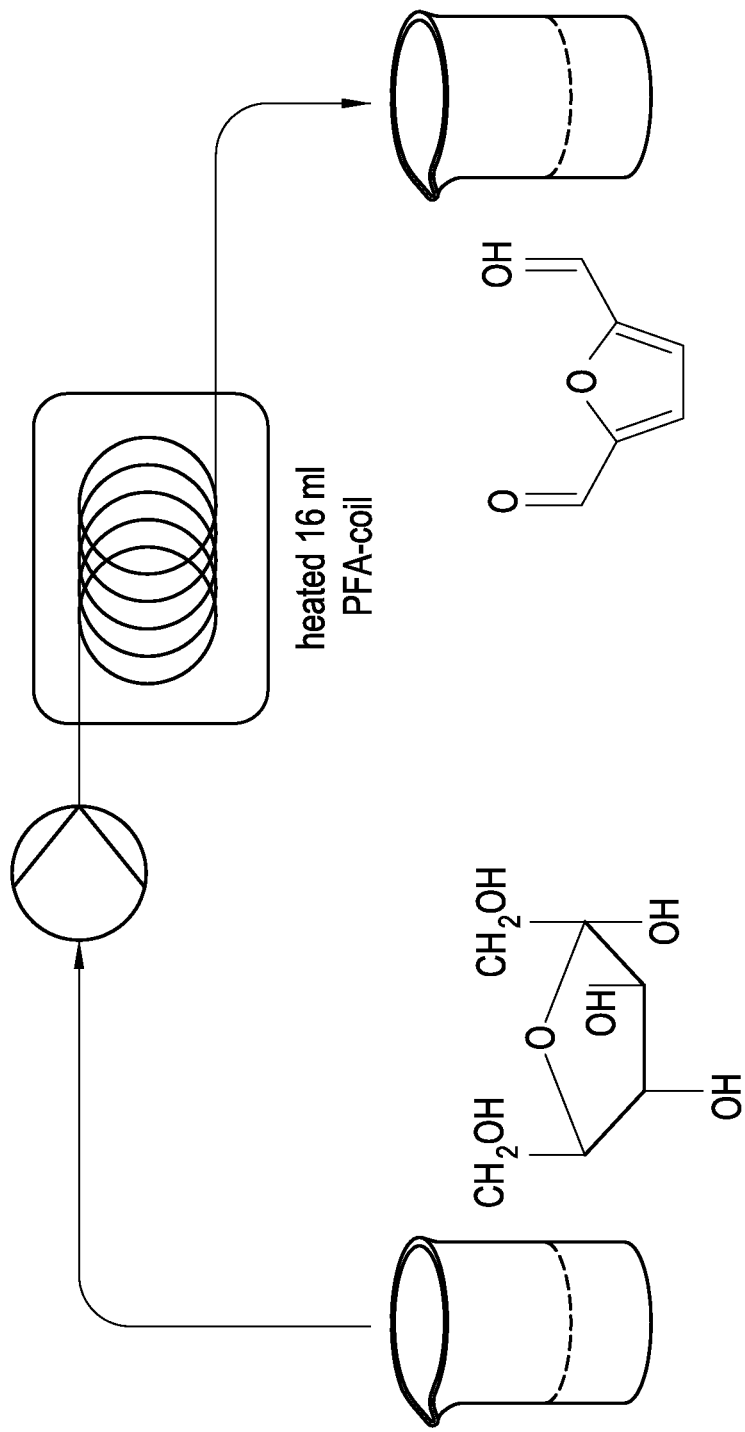
FIG. 9
shows a schematic reaction set-up for stopped flow microwave reactions and continuous flow reactions for the production of furan derivatives from D-fructose In the following examples all temperatures are in degrees Celsius (° C.). The following abbreviations are used:
EtOAc ethyl acetate
FDCA furan dicarboxylic acid
h hour(s)
HMF 5-hydroxymethylfurfural
HPLC high-performance liquid chromatography
IPA isopropyl alcohol (2-propanol)
LS levulinic acid
MeOH methanol
NMP N-methyl pyrrolidone (N-methyl-2-pyrrolidone)
PET polyethylene terephthalate
PEF polyethylene furanoate
RT room temperature
SILP Supported Ionic Liquid Phase
TFA trifluoroacetic acid

Alternatively, a perfluoroalkoxy alkane capillary was used (PFA capillary, inner diameter of 0.8 mm, outer diameter of 1.6 mm), which was wound around a heatable aluminium cylinder. The substrates were added at a desired flow rate by means of a Shimadzu LC-10AD HPLC pump. Exact volumes (column 16.0 mL; dead volume before and after the column, in each case, 1.0 mL) were determined by tracing defined flow rates of the pure solvent with a digital time clock. The reaction set-up is illustrated in FIG. 9.

Analysis of the Reactions for the Conversion of D-Fructose into Furan Derivatives For a quantitative HPLC analysis, samples of the reaction samples (22 μL, unless specified otherwise) were diluted to 1 mL with deionized water. In reaction samples exhibiting a different concentration, the dilution was adjusted such that the maximum concentration did not exceed 2 mg/ml.

100 μL of 3-hydroxybenzyl alcohol were added to said solution as an internal standard, whereupon the sample was mixed thoroughly. Solid residues were separated by centrifugation (5 min, 20000 G) or filtration (Phenex PTFE, 4 mm, 0.2 μm). Quantification was effected on the basis of the areas of the peaks in the RI-spectrum in comparison to the internal standard. The samples were analyzed via HPLC on a Thermo Scientific® Surveyor Plus System or a Shimadzu® Nexera System, each equipped with PDA Plus- and RI detectors. For the separation, an ion exclusion column from Phenomenex® (Rezex RHM-Monosaccharide H+ (8%), 150×7.8 mm, composed of a crosslinked matrix of sulfonated styrol and divinylbenzol, H+-form) was used as a stationary phase, and a solvent mixture of water (HPLC-grade) and 0.1% TFA (HPLC-grade) was used as an eluent. The column temperature was kept constant and at 85° C., while the running time was optimized to 25 minutes. Product quantification was performed based on an internal standard by integrating the RI signal. Via PDA, the wavelengths 200 nm, 254 nm and 280 nm were additionally recorded for a further reaction analysis.

GP1—D-Fructose Dehydration in a Batch Process

In a standard reaction for optimizing the reaction, 100 mg of D-fructose (0.56 mmol) and the respective catalyst were placed in a desired amount into a glass vial and mixed with 1 mL of freshly distilled NMP. The obtained solution/suspension was heated to the chosen temperature and allowed to react for the desired time.

GP2—D-Fructose Dehydration in a Microwave Batch Process

In a standard reaction for optimizing the reaction, 100 mg of D-fructose (0.56 mmol) and the respective catalyst were placed in a desired amount into a microwave vessel (0.5-2.0 mL). The vessel was equipped with a magnetic stirring bar and filled up with 1 mL NMP. The radiation intensity of the microwave was adjusted automatically by a company-owned regulation algorithm in order to reach the desired temperature. Rapid cooling of the reaction vessel was realized with pressurized air of at least 6 bar which was injected.

GP 3—D-Fructose Dehydration in a Microwave Stopped Flow Process

In a standard reaction for optimizing the reaction, a D-fructose standard solution (1 mL; c=100 mg/mL in NMP) and hydrochloric acid (100 μL; c=1 mol/L) were filled into a microwave vessel and equipped with a magnetic stirring bar. After sealing the vial with a Snap-Cap, the solution was heated to the desired temperature for the desired time. In order to effect the fastest possible heating, the supplied energy was adjusted according to the following Table 1.

TABLE 1

Power adjustment of the microwave and associated temperatures

| temperature | power adjustment |
| --- | --- |
| 100° C. | 50 W |
| 125° C. | 65 W |
| 150° C. | 100 W |
| 180° C. | 125 W |
| 200° C. | 140 W |
| 220° C. | 160 W |

Rapid cooling of the reaction vessel was realized with pressurized air of at least 6 bar which was injected.

GP4—D-Fructose Dehydration in a Cartridge-Based Reactor System

In a standard reaction for optimizing the reaction, a D-fructose standard solution (1 mL; c=100 mg/mL in NMP) was mixed with hydrochloric acid (c=1 mol/L) and pumped into the reaction system through a reagent pump. During the heating process, several preliminary samples were taken in order to monitor a stable temperature and a stable flow rate. 150° C., 180° C. and 200° C. were chosen as reaction temperatures, whereas the reaction pressure was set to 40 bar. For this purpose, flow rates of between 0.2 and 0.6 ml/min were chosen. Reaction samples were collected in amounts of 2.5 mL and analyzed.

Example 5

Use of Sulphuric Acid as a Catalyst for the Dehydration of D-Fructose

Different temperatures, reaction times and acid concentrations were compared. The reactions were performed according to "GP1" (Example 4). Either 100 μl of 1 N sulphuric acid or 10 μl of concentrated sulphuric acid was used as a catalyst. In Table 2, the results are summarized.

TABLE 2

Sulphuric acid as a catalyst for the dehydration of D-fructose

| catalyst | temperature | reaction time | fructose consumption | HMF yield | HMF selectivity | LS yield |
| --- | --- | --- | --- | --- | --- | --- |
| 1N H$_2$SO$_4$ | 100° C. | 3 h | 69% | 45% | 65% | <1% |
| 1N H$_2$SO$_4$ | 120° C. | 4 h | 95% | 77% | 81% | <1% |
| 1N H$_2$SO$_4$ | 150° C. | 15 min | 98% | 88% | 90% | <1% |
| 1N H$_2$SO$_4$ | 180° C. | 10 min | 100% | 85% | 85% | <1% |
| H$_2$SO$_4$ conc. | 120° C. | 45 min | 98% | 85% | 90% | <1% |

TABLE 2-continued

Sulphuric acid as a catalyst for the dehydration of D-fructose

| catalyst | temperature | reaction time | fructose consumption | HMF yield | HMF selectivity | LS yield |
|---|---|---|---|---|---|---|
| $H_2SO_4$ conc. | 150° C. | 10 min | 100% | 90% | 90% | <1% |
| $H_2SO_4$ conc. | 180° C. | 5 min | 100% | 82% | 82% | <1% |

A formation of black insoluble polymers and humines was not observed under the optimum conditions which were employed. For analyzing the course of the reaction, a time series for a representative reaction was included ($H_2SO_4$ conc., 150° C., see FIG. 1).

Example 6

Use of Chrome-(II)-Chloride as a Catalyst for the Dehydration of D-Fructose

As described by Zhao, H.; Holladay, J. E.; Brown, H.; Zhang, Z. C. Science 2007, 316, 1597-1600, chrome-(II)-chloride may be used as an effective catalyst for the dehydration of D-fructose. In said example, the effect $CrCl_2$ in N-methyl-2-pyrrolidone is shown. The experiments were conducted according to Provision "GP1" (Example 4). While relatively low yields of HMF were achieved, significant amounts of tar-like compounds could be observed (Table 3).

TABLE 3

Chrome-(II)-chloride as a catalyst for the dehydration of D-fructose

| amount of catalyst | temp. | reaction time | fructose consumption | HMF yield | HMF selectivity | LS yield |
|---|---|---|---|---|---|---|
| 10 mg $CrCl_2$ | 100° C. | 3 h | 86% | 51% | 59% | <1% |
| 10 mg $CrCl_2$ | 150° C. | 3 h | 100% | 39% | 39% | <1% |

Example 7

Use of Montmorillonite KSF® as a Catalyst for the Dehydration of D-Fructose 100 mg of D-fructose was incubated in the presence of 1 ml N-methyl-2-pyrrolidone while being stirred (Provision "GP1", Example 4). 3 h was consistently chosen as the reaction time. In doing so, different amounts of Montmorilonite KSF® were added as a catalyst. Table 4 summarizes the results. Under the best conditions, an HMF yield of 61% with an HMF selectivity of 63% could be achieved.

TABLE 4

Montmorillonite KSF ® as a catalyst for the dehydration of D-fructose

| catalyst | temp. | fructose consumption | HMF yield | HMF selectivity | LS yield | tar |
|---|---|---|---|---|---|---|
| 1 mg | 120° C. | 37% | 11% | 31% | <1% | no |
| 3 mg | 120° C. | 54% | 20% | 38% | <1% | no |
| 5 mg | 120° C. | 65% | 30% | 46% | <1% | no |
| 7 mg | 120° C. | 73% | 32% | 44% | <1% | no |
| 10 mg | 120° C. | 80% | 41% | 52% | <1% | no |
| 20 mg | 120° C. | 90% | 43% | 48% | <1% | no |
| 40 mg | 120° C. | 94% | 43% | 46% | <1% | no |
| 1 mg | 130° C. | 31% | 11% | 35% | <1% | no |
| 3 mg | 130° C. | 73% | 35% | 48% | <1% | no |
| 5 mg | 130° C. | 87% | 46% | 53% | <1% | no |
| 7 mg | 130° C. | 92% | 50% | 55% | <1% | no |
| 10 mg | 130° C. | 94% | 49% | 52% | <1% | no |
| 20 mg | 130° C. | 96% | 54% | 57% | <1% | no |
| 40 mg | 130° C. | 97% | 54% | 55% | <1% | yes |
| 1 mg | 140° C. | 72% | 30% | 42% | <1% | no |
| 3 mg | 140° C. | 91% | 46% | 51% | <1% | no |
| 5 mg | 140° C. | 95% | 53% | 56% | <1% | no |
| 7 mg | 140° C. | 96% | 53% | 55% | <1% | no |
| 10 mg | 140° C. | 98% | 55% | 56% | <1% | no |
| 20 mg | 140° C. | 98% | 56% | 57% | <1% | no |
| 40 mg | 140° C. | 99% | 56% | 56% | <1% | yes |
| 1 mg | 150° C. | 94% | 44% | 46% | <1% | no |
| 3 mg | 150° C. | 96% | 52% | 54% | <1% | no |
| 5 mg | 150° C. | 98% | 56% | 57% | <1% | no |
| 7 mg | 150° C. | 98% | 57% | 59% | <1% | no |
| 10 mg | 150° C. | 98% | 58% | 59% | <1% | yes |
| 20 mg | 150° C. | 97% | 61% | 63% | <1% | yes |
| 40 mg | 150° C. | 97% | 61% | 63% | <1% | yes |

Example 8

Use of Amberlite 150 as a Catalyst for the Dehydration of D-Fructose

This example shows the use of a strong ion exchanger with sulfonic acid residues based on a macro-crosslinked resin. 100 mg of D-fructose were incubated in the presence of 1 ml N-methyl-2-pyrrolidone at 100° C. for 3 h, while being stirred (Provision "GP1", Example 4). Amberlite 15® was thereby added as a catalyst. In Table 5, the result of said experiment is shown. In contrast to Montmorillonite KSF®, a higher yield could be obtained at the relatively low temperature. The formation of tar-like compounds was avoided.

TABLE 5

Amberlite 15 ® as a catalyst for the dehydration of D-fructose

| amount of catalyst | temp. | reaction time | fructose consumption | HMF yield | HMF selectivity | LS yield |
|---|---|---|---|---|---|---|
| 10 mg | 100° C. | 3 h | 70% | 50% | 71% | <1% |

Example 9

Use of $SiO_2$—$MgCl_2$ as a Catalyst for the Dehydration of D-Fructose

Since a silica gel-magnesium chloride-complex displayed a catalytic activity during the dehydration of carbohydrates in acetonitrile (Yasuda, M.; Nakamura, Y.; Matsumoto, J.; Yokoi, H. Shiragami, T. Bull. Chem. Soc. Jpn. 2011, 84, 416-418), said catalyst was tested for its suitability in N-methyl-2-pyrrolidone. Under reaction conditions as in "GP1" (Example 4), a yield of 26% HMF was achieved in the best case (see Table 6). However, if merely a silica gel was used, the yield fell to below 1%. The formation of large amounts of tar-like compounds was thereby observed.

TABLE 6

SiO$_2$—MgCl$_2$ as a catalyst for the dehydration of D-fructose

| amount of catalyst | temp. | reaction time | fructose consumption | HMF yield | HMF selectivity | LS yield |
|---|---|---|---|---|---|---|
| 200 mg | 150° C. | 30 min | 99% | 26% | 26% | 4% |

Example 10

Use of AlCl$_3$ as a Catalyst for the Dehydration of D-Fructose

AlCl$_3$ was tested under reaction conditions "GP1" (Example 4) as an example of a Lewis acid catalyst. Freshly sublimated AlCl$_3$ was used for this purpose. Similar results as with Amberlite 15® were achieved. However, the catalyst is sensitive to hydrolysis and thus cannot be used for repeated applications or in continuous processes. In addition, relatively large amounts of tar-like compounds were formed (for the result, see Table 7).

TABLE 7

AlCl$_3$ as a catalyst for the dehydration of D-fructose

| amount of catalyst | temp. | reaction time | fructose consumption | HMF yield | HMF selectivity | LS yield |
|---|---|---|---|---|---|---|
| 10 mg | 100° C. | 3 h | 100% | 50% | 50% | <1% |

Example 11

Use of SILPs Combined with Chrome-(II)-Chloride as a Catalyst for the Dehydration of D-Fructose A combination of CrCl$_2$ and SILPs (silica-supported ionic liquid phase, see Example 4) was tested, wherein the reaction conditions "GP1" (Example 4) were applied. After 20 min, a yield of almost 50% HMF could be achieved. This, however, could not be increased with longer reaction times. Furthermore, a conversion of D-fructose into D-glucose could be detected with shorter reaction times (Table 8).

TABLE 8

SILPs combined with CrCl$_2$ as a catalyst for the dehydration of D-fructose

| temp. | reaction time | fructose consumption | glucose yield | HMF yield | HMF selectivity | LS yield |
|---|---|---|---|---|---|---|
| 120° C. | 5 min | 85% | 5% | 39% | 46% | <1% |
| 120° C. | 10 min | 94% | 3% | 45% | 48% | <1% |
| 120° C. | 15 min | 99% | 1% | 44% | 45% | <1% |
| 120° C. | 20 min | 97% | 2% | 49% | 51% | <1% |
| 120° C. | 25 min | 97% | 1% | 47% | 48% | <1% |
| 120° C. | 30 min | 98% | <1% | 49% | 50% | <1% |
| 120° C. | 45 min | 99% | <1% | 48% | 49% | <1% |
| 120° C. | 1 h | 99% | <1% | 52% | 52% | <1% |

Example 12

Use of Sulphuric Acid as a Catalyst for the Dehydration of D-Fructose (Microwave Heating)

Figure 2:
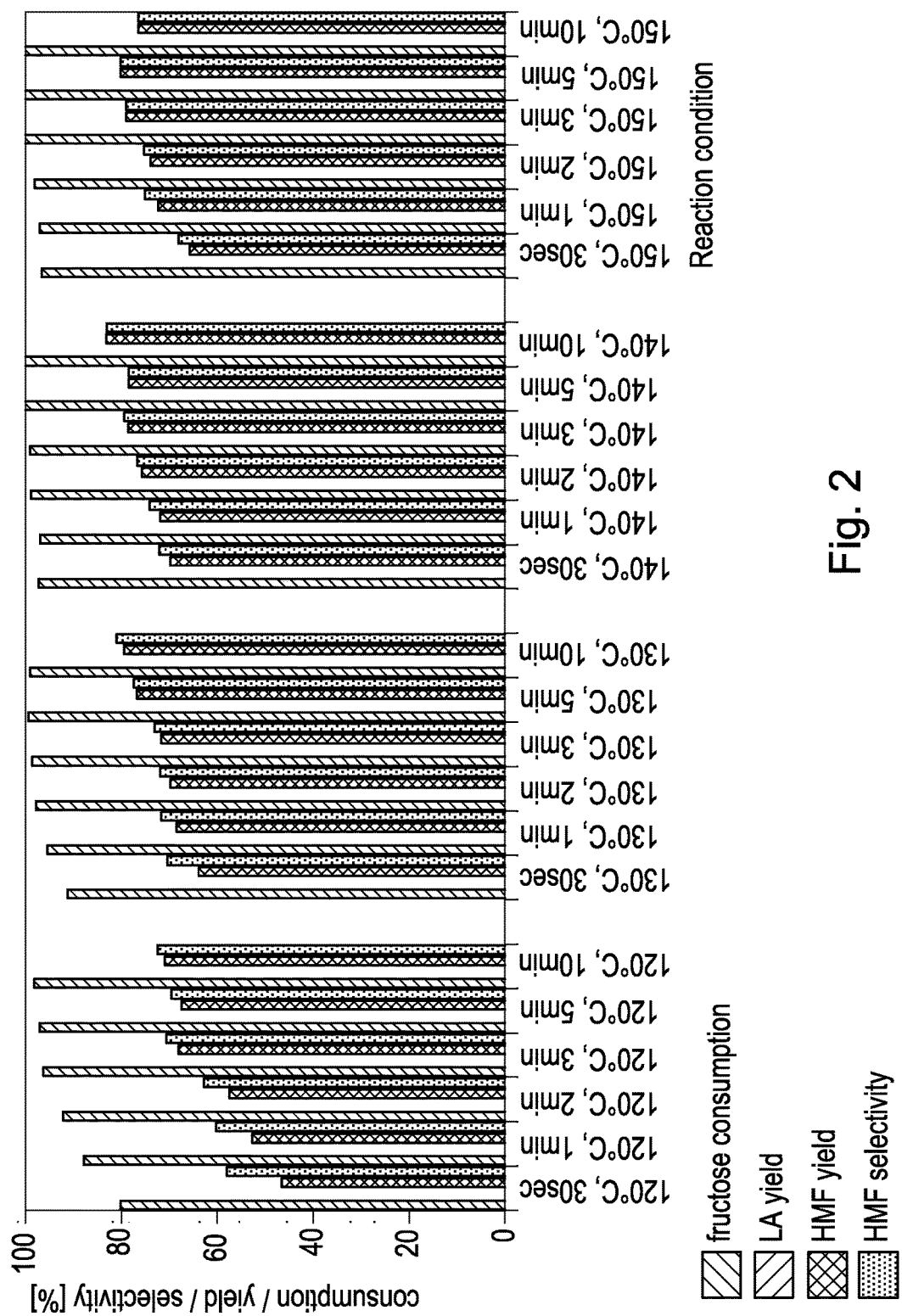
FIG. 2 and FIG. 3
show results in the dehydration of D-fructose in N-methyl-2-pyrrolidone, with sulphuric acid as a catalyst—implementation in the microwave reactor according to Example 12
Figure 3:
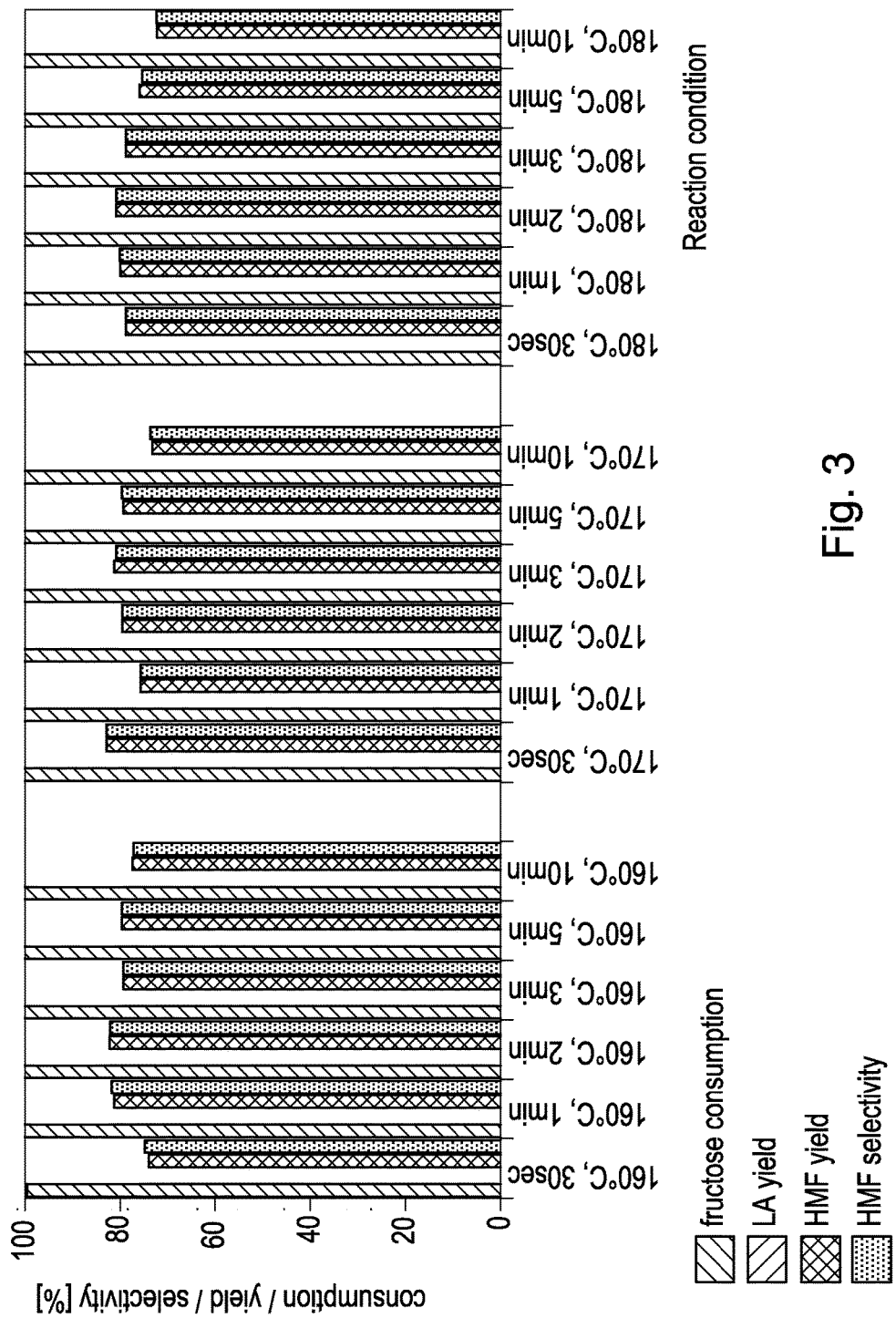

In order to achieve a better control over the heating phase and the cooling phase as well as over the reaction temperature, a microwave-based system was used for adjusting the temperature. Using N-methyl-2-pyrrolidone, samples were prepared as specified in Provision "GP2" (Example 4). No formation of tar-like compounds was detected under the reaction conditions which were applied. A complete conversion of D-fructose and a yield of 83% HMF could maximally be achieved (FIG. 2 and FIG. 3).

Example 13

Use of Hydrochloric Acid as a Catalyst for the Dehydration of D-Fructose (Microwave Heating)

Figure 4:
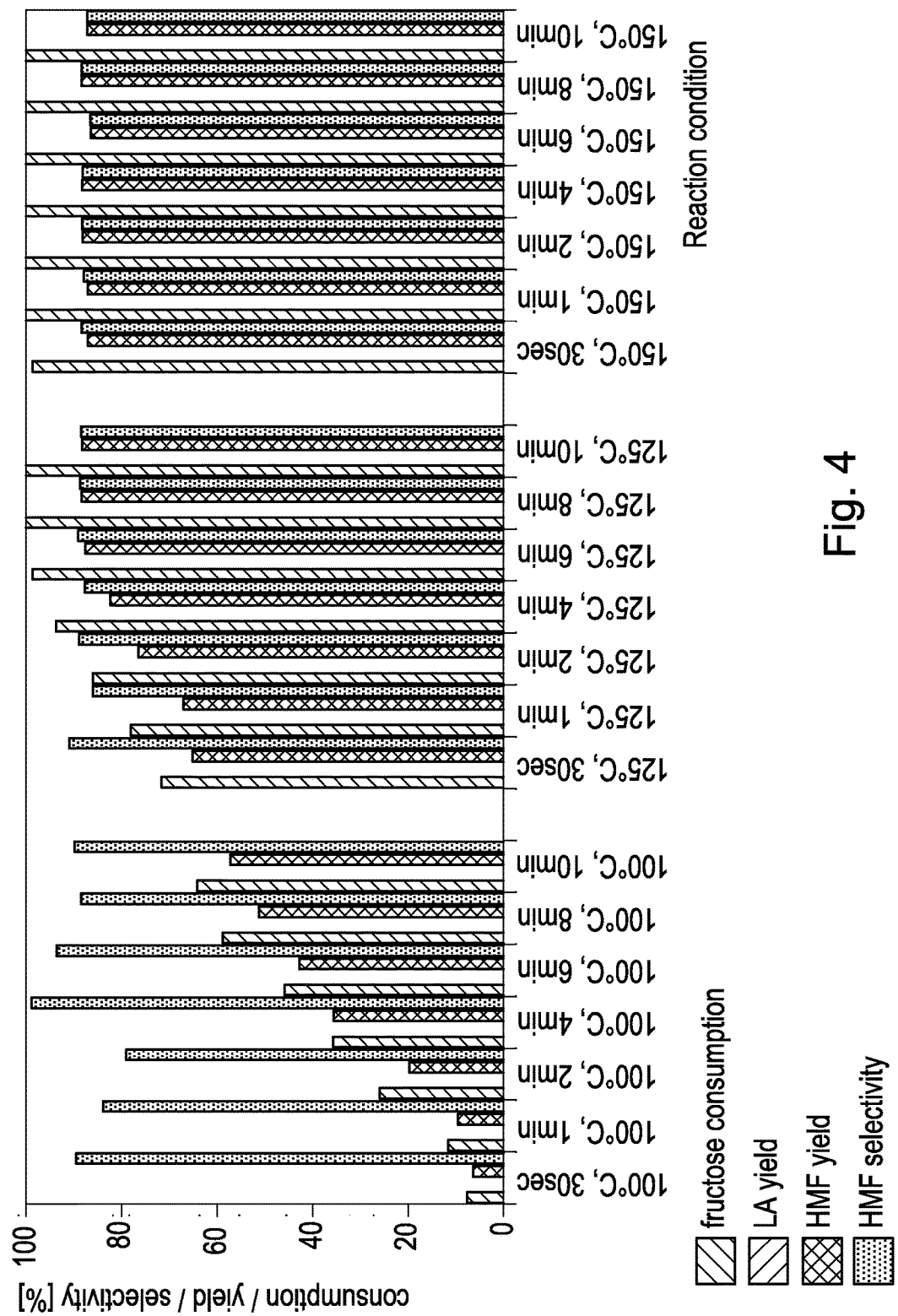
FIG. 4 and FIG. 5
show results in the dehydration of D-fructose in N-methyl-2-pyrrolidone, with hydrochloric acid as a catalyst—implementation in the microwave reactor according to Example 13
Figure 5:
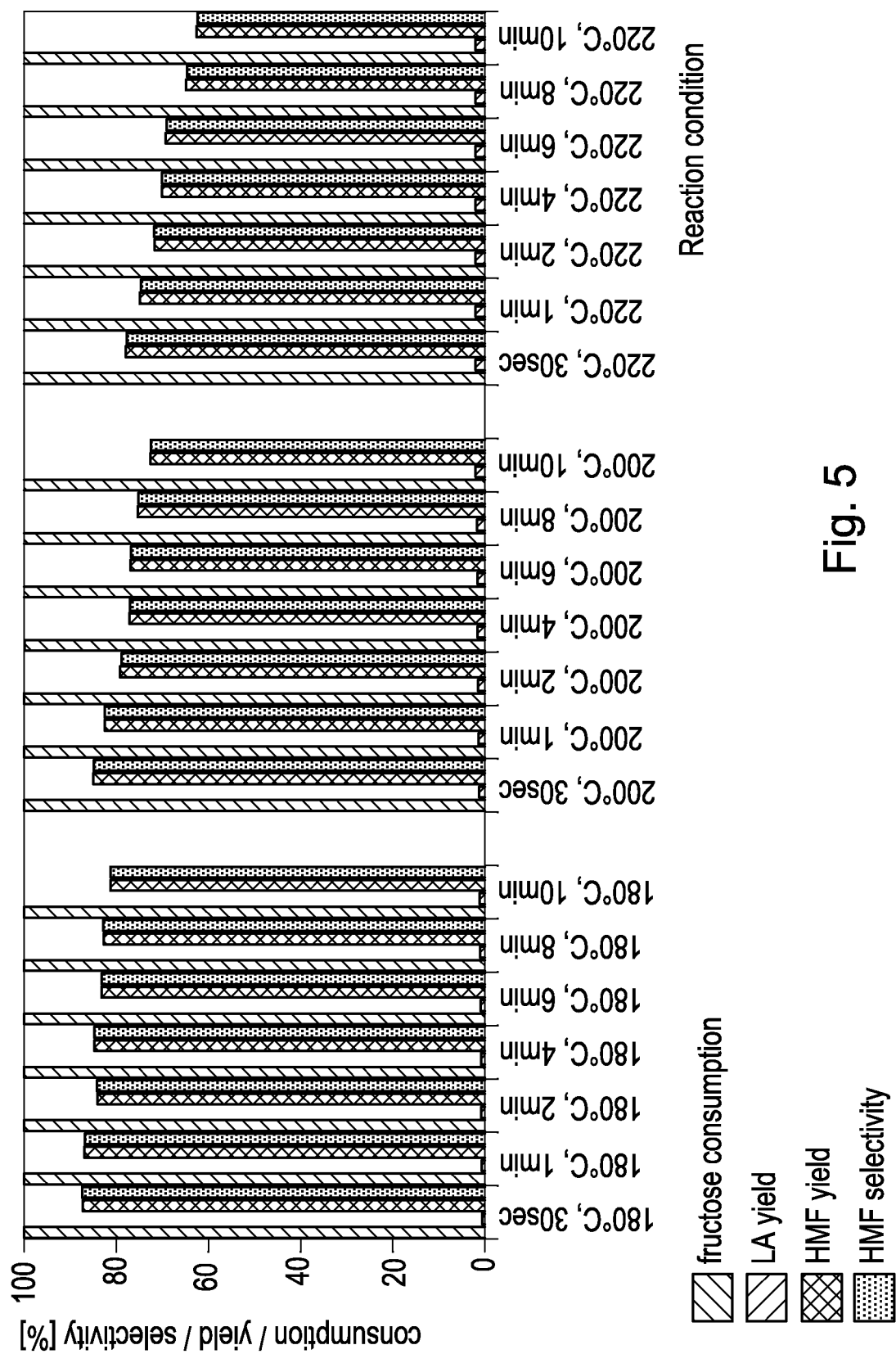

The dehydration of D-fructose was performed in a stopped-flow microwave reactor according to Provision "GP3" (Example 4). Higher temperatures were necessary for achieving a complete conversion of D-fructose. While, at lower temperatures, longer reaction times improved the yield of HMF, the latter decreased at higher temperatures with an increasing reaction time (FIGS. 4 and 5). With a complete conversion of D-fructose, a maximum yield of 89% HMF could be achieved.

Example 14

Use of Montmorillonite KSF® as a Catalyst for the Dehydration of D-Fructose (Microwave Heating)

Since a rapid heating/cooling as well as a very good control of the temperature in the reaction vessel can be effected with microwave methods, the heterogeneous catalyst Montmorillonite KSF® was also used for the dehydration of D-fructose in N-methyl-2-pyrrolidone. Reaction conditions according to "GP2" (Example 4) were employed. The reaction time amounted to 5 min. Although only comparatively low D-fructose conversions and HMF yields were achieved, the formation of tar-like compounds could be avoided (for the results, see Table 9).

TABLE 9

Montmorillonite KSF ® as a catalyst for the dehydration of D-fructose (microwave heating)

| amount of catalyst | temp. | fructose consumption | HMF yield | HMF selectivity | LS yield | tar |
|---|---|---|---|---|---|---|
| 5 mg | 150° C. | 51% | 20% | 39% | <1% | no |
| 7 mg | 150° C. | 61% | 26% | 43% | <1% | no |
| 10 mg | 150° C. | 64% | 30% | 46% | <1% | no |
| 15 mg | 150° C. | 76% | 38% | 50% | <1% | no |
| 20 mg | 150° C. | 82% | 43% | 52% | <1% | no |

Figure 6:
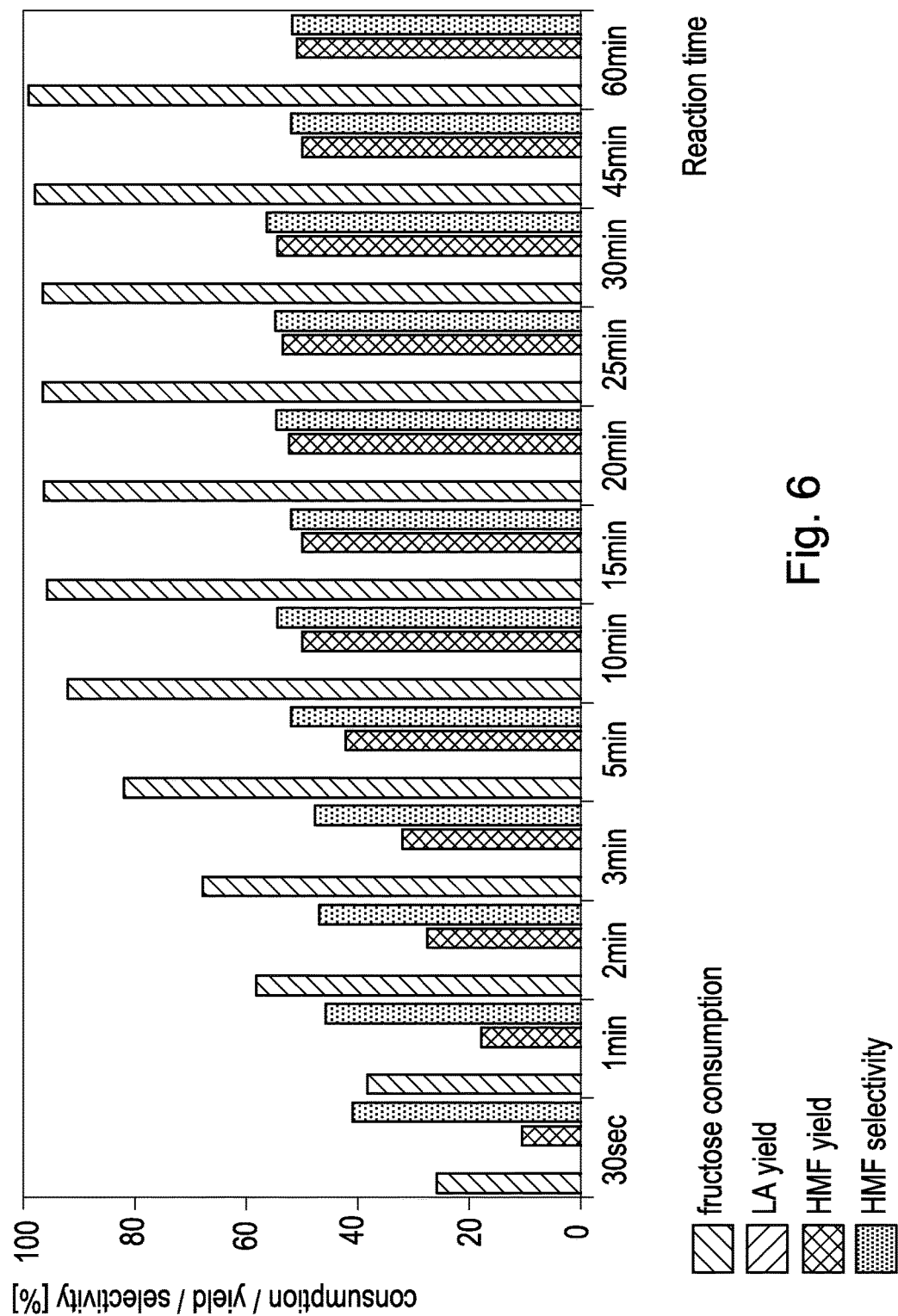
FIG. 6
shows results in the dehydration of D-fructose in N-methyl-2-pyrrolidone, with Montmorillonite KSF® as a catalyst—implementation in the microwave reactor according to Example 14

In order to find the best reaction conditions, different reaction times were tested at 150° C., using 20 mg of a catalyst (FIG. 6).

Example 15

Use of Sulphuric Acid for Catalyzing the Conversion of D-Fructose into Furan Derivatives (Continuous Process)

D-Fructose (10% w/v) and concentrated sulphuric acid (1% v/v) were dissolved in N-methyl-2-pyrrolidone. The mixture was pumped through the reactor by means of a PFA capillary with a continuous flow (reaction temperature 150° C.). After the first 18 ml had been discarded, another 10 ml was collected for the analysis. By way of a number of flow rates, the effect of different residence times in the reactor was tested (Table 10).

TABLE 10

Sulphuric acid for catalyzing the conversion of D-fructose into furan derivatives (continuous process)

| flow rate (ml/min) | residence time | fructose consumption | HMF yield | HMF selectivity | LS yield |
|---|---|---|---|---|---|
| 0.8 ml/min | 20 min | 100% | 74% | 74% | <1% |
| 1.6 ml/min | 10 min | 100% | 75% | 75% | <1% |
| 3.2 ml/min | 5 min | 100% | 76% | 76% | <1% |

No formation of black insoluble polymers and humines was observed under the tested conditions.

Example 16

Use of Hydrochloric Acid for Catalyzing the Conversion of D-Fructose into Furan Derivatives (Continuous Process)

Figure 7:
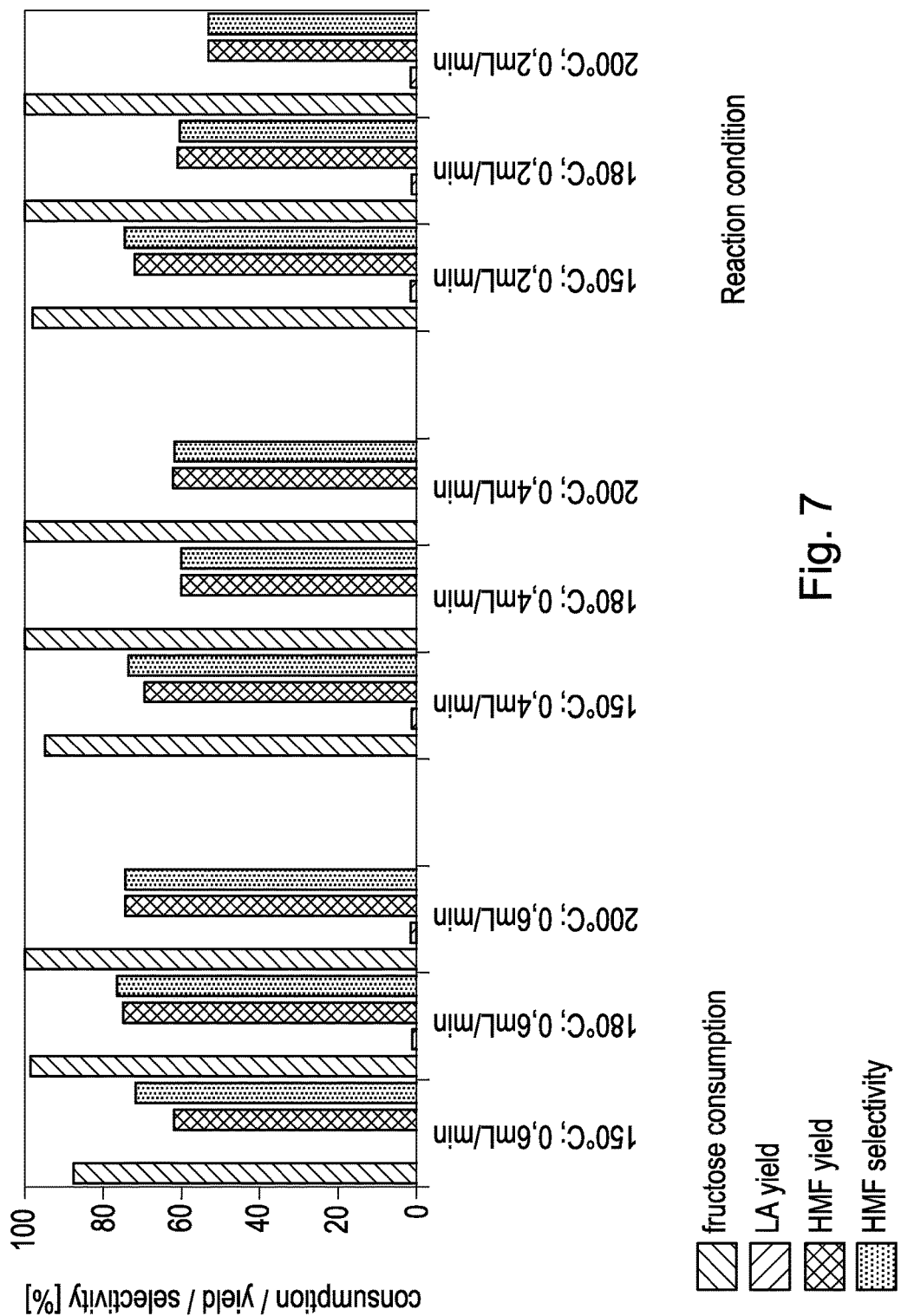
FIG. 7
show results in the dehydration of D-fructose in N-methyl-2-pyrrolidone, with hydrochloric acid as a catalyst—reaction in the flow reactor according to Example 15

In that example, hydrochloric acid was used as a catalyst for the dehydration of D-fructose in NMP under a continuous flow (for the reaction conditions, see Provision "GP4", Example 4). A maximum yield of 75% HMF could be achieved at a reaction temperature of 180° C. and a flow of 0.6 ml/min. A selectivity of 76% HMF was thereby achieved. In most cases, the proportion of levulinic acid (LS) was below 1% (for the results, see FIG. 7).

The invention claimed is:

1. A method for producing furan derivatives from D-glucose, comprising:
    A) converting D-glucose to D-Fructose in a multi-step reaction carried out in a reaction mixture comprising, as product-forming reactants, D-glucose, xylose reductase, sorbitol dehydrogenase, and two or more redox cofactors selected from NAD⁺/NADH and/or NADP⁺/NADPH, and wherein the multi-step reaction comprises:
        1) the xylose reductase and NADH or NADPH reducing at least a portion of the D-glucose to D-sorbitol and forming oxidized NAD⁺ or NADP⁺ in the reaction mixture; and
        2) the sorbitol dehydrogenase and NAD⁺ or NADP⁺ oxidizing at least a portion of the D-sorbitol to D-fructose and forming reduced NADH or NADPH in the reaction mixture; and
    B) converting at least a portion of the D-fructose formed in A) into one or more furan derivatives selected from hydroxymethylfurfural, 2,5-furan dicarboxylic acid, and polymerization products thereof.

2. The method of claim 1, the multi-step reaction of A) further comprising:
    3) regenerating the NADH or NADPH by the NAD⁺ or NADP⁺ formed in 1) and a first regenerating oxidoreductase and oxidizing a first redox cosubstrate in the reaction mixture; and
    4) regenerating the NAD⁺ or NADP⁺ by the NADH or NADPH formed in 2) and a second regenerating oxidoreductase and reducing a second redox cosubstrate in the reaction mixture.

3. The method of claim 2, wherein the first and second regenerating oxidoreductases are selected from the group consisting of dehydrogenases, reductases, oxidases and catalases.

4. The method of claim 3, wherein the first and second regenerating oxidoreductases are selected from the group consisting of alcohol dehydrogenases, NADH oxidases, hydrogenases, lactate dehydrogenases, formate dehydrogenases, and oxaloacetate-decarboxylating malate dehydrogenases.

5. The method of claim 2, wherein the first cosubstrate is selected from the group consisting of alcohols, 2-propanol, lactic acid, salts of lactic acid, formic acid, salts of formic acid, malic acid, salts of malic acid, and hydrogen.

6. The method of claim 2, wherein the first cosubstrate comprises a ($C_4$-$C_8$)-cycloalkanol or a compound of general formula II:

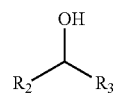

II wherein $R_2$ and $R_3$ are independently selected from the group consisting of H, ($C_1$-$C_6$)-alkyl, wherein alkyl is linear-chain or branched, ($C_1$-$C_6$)-alkenyl, wherein alkenyl is linear-chain or branched and contains one to three double bonds, aryl, $C_6$-$C_{12}$-aryl, carboxyl, ($C_1$-$C_4$)-carboxyalkyl, cycloalkyl, and $C_3$-$C_8$-cycloalkyl.

7. The method of claim 2, wherein the second cosubstrate is selected from the group consisting of pyruvic acid, salts of pyruvic acid, and oxygen.

8. The method of claim 2, wherein the second cosubstrate comprises oxygen or a compound of general formula I:

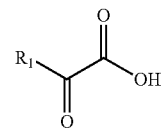

I wherein $R_1$ is a linear-chain or branched ($C_1$-$C_4$)-alkyl group or a ($C_1$-$C_4$)-carboxyalkyl group.

9. The method of claim 1, wherein the D-sorbitol formed in A) is not isolated.

10. The method of claim 1, wherein the redox cofactors are provided in soluble form and/or are immobilized onto solids.

11. The method of claim 1, wherein A) proceeds according to the following reaction scheme:

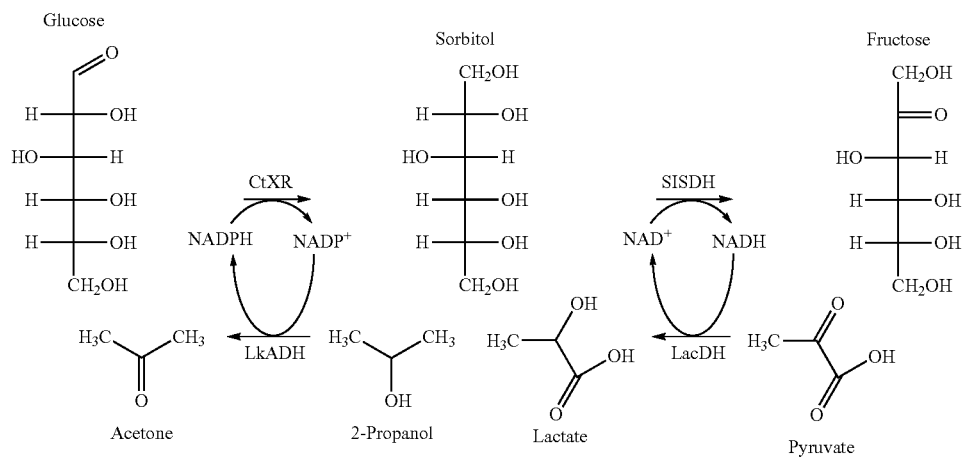

wherein
CtXR = xylose reductase from *Candida tropicalis*
SlSDH = sorbitol dehydrogenase from sheep liver
LkADH = alcohol dehydrogenase from *Lactobacillus kefir*, NADP(H)-Dependent
LacDH = lactate dehydrogenase, NAD(H)-dependent.

12. The method of claim 1, wherein A) proceeds according to the following reaction scheme:

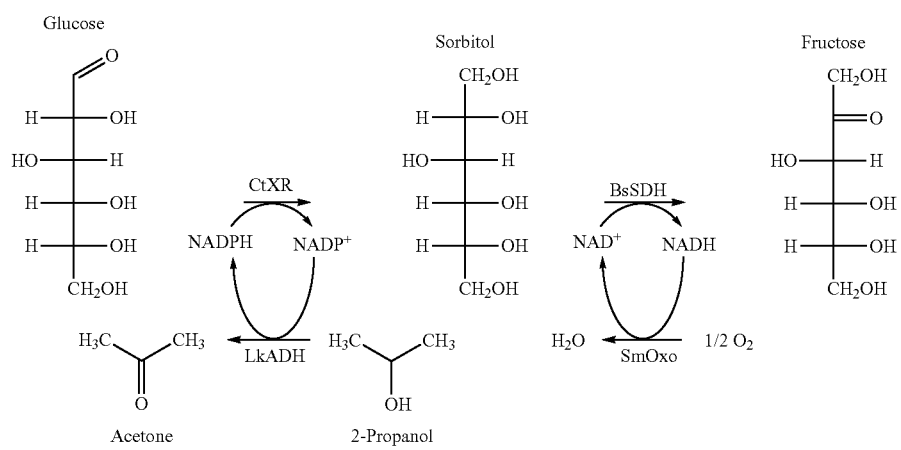

wherein
CtXR = xylose reductase from *Candida tropicalis*
BsSDH = sorbitol dehydrogenase from *Bacillus subtilis*
LkADH = alcohol dehydrogenase from *Lactobacillus kefir*, NADP(H)-Dependent
SmOxo = NADH oxidase from *Streptococcus mutans*.

13. The method of claim 1, further comprising isolating the D-fructose formed in A).

14. The method of claim 13, wherein the D-fructose is isolated in crystalline form.

15. The method of claim 13, wherein B) comprises reacting the D-fructose with an acidic catalyst and a solvent.

16. The method of claim 15, wherein the solvent comprises N-methyl-2-pyrrolidone of formula

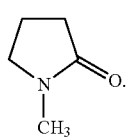

17. The method of claim 16, wherein the N-methyl-2-pyrrolidone is used either as a reaction solvent or as a co-solvent.

18. The method of claim 13, wherein B) is performed as a batch method.

19. The method of claim 18, wherein the batch method is performed under microwave heating.

20. The method of claim 13, wherein B) is performed as a continuous method.

21. The method of claim 20, wherein the continuous method is performed under microwave heating.

22. The method of claim 13, wherein B) is performed using at least one acid catalyst selected from the group consisting of a homogeneous acid catalyst, a heterogeneous acid catalyst, a Lewis acid catalyst, and a silica supported ionic liquid phase (SILP) catalyst.

23. The method of claim 22, wherein the acid catalyst is a homogeneous acid catalyst comprising at least one of sulphuric acid or hydrochloric acid.

24. The method of claim 22, wherein the acid catalyst is a heterogeneous acid catalyst comprising at least one of an ion exchanger, montmorillonite, or ion exchange resin.

25. The method of claim 22, wherein the acid catalyst is a Lewis acid catalyst comprising at least one of $CrCl_2$, $AlCl_3$ or $SiO_2$—$MgCl_2$.

26. A method for producing furan derivatives from D-glucose, comprising:
A) converting D-glucose to D-Fructose in a multi-step reaction carried out in a reaction mixture comprising, as product-forming reactants, D-glucose, xylose reductase, sorbitol dehydrogenase, and two or more redox cofactors selected from $NAD^+$/NADH and/or $NADP^+$/NADPH, and wherein the multi-step reaction comprises:
1) the xylose reductase and NADH or NADPH reducing at least a portion of the D-glucose to D-sorbitol and forming oxidized $NAD^+$ or $NADP^+$ in the reaction mixture;
2) the sorbitol dehydrogenase and $NAD^+$ or $NADP^+$ oxidizing at least a portion of the D-sorbitol to D-fructose and forming reduced NADH or NADPH in the reaction mixture;
3) regenerating the NADH or NADPH in the reaction mixture by the $NAD^+$ or $NADP^+$ formed in 1) and a first regenerating oxidoreductase selected from the group consisting of dehydrogenases, reductases, oxidases and catalases oxidizing a first redox cosubstrate selected from the group consisting of alcohols, 2-propanol, lactic acid, salts of lactic acid, formic acid, salts of formic acid, malic acid, salts of malic acid, hydrogen, $(C_4$-$C_8)$-cycloalkanols, and compounds of general formula II:

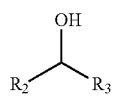

wherein $R_2$ and $R_3$ are independently selected from the group consisting of H, $(C_1$-$C_6)$-alkyl, wherein alkyl is linear-chain or branched, $(C_1$-$C_6)$-alkenyl, wherein alkenyl is linear-chain or branched and contains one to three double bonds, aryl, $C_6$-$C_{12}$-aryl, carboxyl, $(C_1$-$C_4)$-carboxyalkyl, cycloalkyl, and $C_3$-$C_8$-cycloalkyl, and wherein the first redox cosubstrate is oxidized; and 4) regenerating the $NAD^+$ or $NADP^+$ in the reaction mixture by the NADH or NADPH formed in 2) and a second regenerating oxidoreductase selected from the group consisting of dehydrogenases, reductases, oxidases and catalases reducing a second redox cosubstrate selected from the group consisting of pyruvic acid, salts of pyruvic acid, oxygen, and compounds of general formula I:

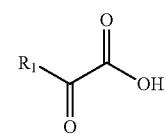

wherein $R_1$ is a linear-chain or branched $(C_1$-$C_4)$-alkyl group or a $(C_1$-$C_4)$-carboxyalkyl group, and wherein the second redox cosubstrate is reduced;

B) isolating the D-fructose formed in A); and

C) reacting the D-fructose isolated in B) with an acidic catalyst and a solvent to convert at least a portion of the D-fructose into one or more furan derivatives.

27. The method of claim 26, wherein the first and second regenerating oxidoreductases are selected from the group consisting of alcohol dehydrogenases, NADH oxidases, hydrogenases, lactate dehydrogenases, formate dehydrogenases, and oxaloacetate-decarboxylating malate dehydrogenases.

28. The method of claim 26, wherein A) proceeds according to the following reaction scheme:

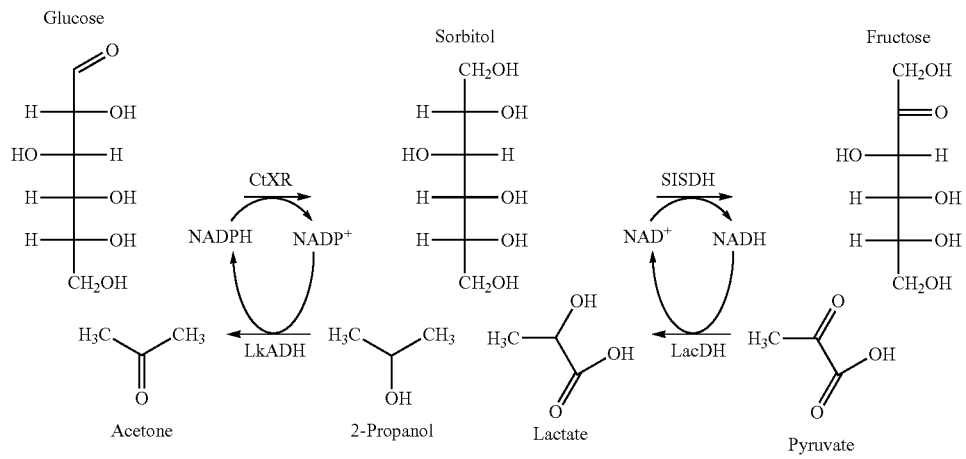

wherein
CtXR = xylose reductase from *Candida tropicalis*
SlSDH = sorbitol dehydrogenase from sheep liver
LkADH = alcohol dehydrogenase from *Lactobacillus kefir*, NADP(H)-Dependent
LacDH = lactate dehydrogenase, NAD(H)-dependent.

29. The method of claim 26, wherein A) proceeds according to the following reaction scheme:
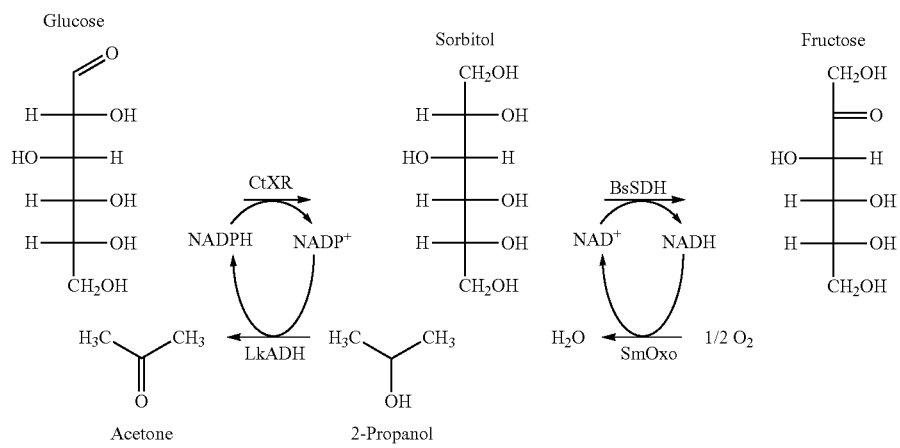
wherein
CtXR = xylose reductase from *Candida tropicalis*
BsSDH = sorbitol dehydrogenase from *Bacillus subtilis*
LkADH = alcohol dehydrogenase from *Lactobacillus kefir*, NADP(H)-Dependent
SmOxo = NADH oxidase from *Streptococcus mutans*.
* * * * *